United States Patent
Perloff et al.

(10) Patent No.: US 12,390,339 B2
(45) Date of Patent: Aug. 19, 2025

(54) EXPANDABLE INTERBODY SPACER

(71) Applicant: GLOBUS MEDICAL, INC., Audubon, PA (US)

(72) Inventors: Jonathan Perloff, Slatington, PA (US); William Rhoda, Media, PA (US); Mark Weiman, Downingtown, PA (US); Chad Glerum, Pennsburg, PA (US); Edward Dwyer, Lehighton, PA (US); Victoria Alexander, Royersford, PA (US); Brian Garvey, Media, PA (US); Daniel Waite, Pottstown, PA (US); Conor Fleming, Media, PA (US); Samuel Petersheim, Elverson, PA (US); Bria Howell, Philadelphia, PA (US); Marcin Niemiec, Norristown, PA (US); Vipin Kunjachan, Norristown, PA (US); Jason Gray, East Greenville, PA (US); Christopher Saville, Morgantown, PA (US); James Himmelberger, Souderton, PA (US); Kevin Gahman, Douglassville, PA (US)

(73) Assignee: Globus Medical Inc., Audubon, PA (US)

( * ) Notice: Subject to any disclaimer, the term of this patent is extended or adjusted under 35 U.S.C. 154(b) by 164 days.

(21) Appl. No.: 18/158,533

(22) Filed: Jan. 24, 2023

(65) Prior Publication Data

US 2023/0157836 A1    May 25, 2023

Related U.S. Application Data

(63) Continuation of application No. 16/660,174, filed on Oct. 22, 2019, now Pat. No. 11,583,409, which is a
(Continued)

(51) Int. Cl.
  *A61F 2/44*    (2006.01)
  *A61B 17/70*   (2006.01)
  (Continued)

(52) U.S. Cl.
  CPC ........ *A61F 2/4425* (2013.01); *A61B 17/7097* (2013.01); *A61F 2/442* (2013.01);
  (Continued)

(58) Field of Classification Search
  CPC .......... A61F 2/44; A61F 2/442; A61F 2/4425; A61F 2/447; A61F 2/46; A61F 2/4611; A61B 17/70; A61B 17/7097
  See application file for complete search history.

(56) References Cited

U.S. PATENT DOCUMENTS

| 4,349,921 A | 9/1982 | Kuntz |
| 4,599,086 A | 7/1986 | Doty |

(Continued)

FOREIGN PATENT DOCUMENTS

| CA | 2088066 A1 | 1/1992 |
| DE | 4012622 C1 | 7/1991 |

(Continued)

*Primary Examiner* — Christopher J Beccia

(57) ABSTRACT

Devices and methods for treating one or more damaged, diseased, or traumatized portions of the spine, including intervertebral discs, to reduce or eliminate associated back pain. In one or more embodiments, the present invention relates to an expandable interbody spacer. The expandable interbody spacer may comprise a first jointed arm comprising a plurality of links pivotally coupled end to end. The expandable interbody spacer further may comprise a second jointed arm comprising a plurality of links pivotally coupled end to end. The first jointed arm and the second jointed arm may be interconnected at a proximal end of the expandable
(Continued)

interbody spacer. The first jointed arm and the second jointed arm may be interconnected at a distal end of the expandable interbody spacer.

15 Claims, 38 Drawing Sheets

Related U.S. Application Data continuation of application No. 15/264,677, filed on Sep. 14, 2016, now Pat. No. 10,485,674, which is a continuation of application No. 13/941,095, filed on Jul. 12, 2013, now Pat. No. 9,480,573, which is a continuation-in-part of application No. 13/483,852, filed on May 30, 2012, now Pat. No. 9,044,342.

(51) Int. Cl.
*A61F 2/46* (2006.01)
*A61F 2/28* (2006.01)
*A61F 2/30* (2006.01)

(52) U.S. Cl.
CPC ............ *A61F 2/4455* (2013.01); *A61F 2/447* (2013.01); *A61F 2/4611* (2013.01); *A61F 2002/2835* (2013.01); *A61F 2002/30108* (2013.01); *A61F 2002/30143* (2013.01); *A61F 2002/30156* (2013.01); *A61F 2002/30159* (2013.01); *A61F 2002/30166* (2013.01); *A61F 2002/30176* (2013.01); *A61F 2002/30189* (2013.01); *A61F 2002/30266* (2013.01); *A61F 2002/30364* (2013.01); *A61F 2002/30365* (2013.01); *A61F 2002/3037* (2013.01); *A61F 2002/30405* (2013.01); *A61F 2002/30433* (2013.01); *A61F 2002/30462* (2013.01); *A61F 2002/30471* (2013.01); *A61F 2002/30484* (2013.01); *A61F 2002/30492* (2013.01); *A61F 2002/305* (2013.01); *A61F 2002/30507* (2013.01); *A61F 2002/30515* (2013.01); *A61F 2002/30518* (2013.01); *A61F 2002/30525* (2013.01); *A61F 2002/3054* (2013.01); *A61F 2002/30545* (2013.01); *A61F 2002/3055* (2013.01); *A61F 2002/30579* (2013.01); *A61F 2002/30581* (2013.01); *A61F 2002/30588* (2013.01); *A61F 2002/30593* (2013.01); *A61F 2002/30624* (2013.01); *A61F 2002/30772* (2013.01); *A61F 2002/30836* (2013.01); *A61F 2002/30892* (2013.01); *A61F 2002/30904* (2013.01); *A61F 2/44* (2013.01); *A61F 2002/4415* (2013.01); *A61F 2002/4627* (2013.01); *A61F 2002/4677* (2013.01); *A61F 2310/00017* (2013.01); *A61F 2310/00023* (2013.01); *A61F 2310/00179* (2013.01)

(56) References Cited

U.S. PATENT DOCUMENTS

| | | |
|---|---|---|
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A * | 3/2000 | Li .............. A61F 2/4455 623/17.16 |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,554,863 B2 | 4/2003 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | Jimenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,044,342 B2 * | 6/2015 | Perloff ............... A61F 2/442 |
| 9,358,125 B2 | 6/2016 | Jimenez et al. |
| 9,532,883 B2 | 1/2017 | McLuen et al. |
| 9,622,878 B2 | 4/2017 | Grotz |
| 2002/0045945 A1 | 4/2002 | Liu |
| 2002/0068976 A1 | 6/2002 | Jackson |
| 2002/0068977 A1 | 6/2002 | Jackson |
| 2003/0176926 A1 | 9/2003 | Boehm et al. |

(56) References Cited

U.S. PATENT DOCUMENTS

| | | |
|---|---|---|
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0243255 A1* | 10/2008 | Butler ................ A61F 2/4465 623/17.11 |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0048676 A1* | 2/2009 | Fabian, Jr. ............ A61F 2/442 623/17.13 |
| 2009/0062833 A1 | 3/2009 | Song |
| 2009/0076616 A1 | 3/2009 | Duggal et al. |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0157084 A1 | 6/2009 | Aalsma et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0123546 A1* | 5/2012 | Medina ................ A61F 2/447 623/17.16 |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010/105181 A1 | 9/2010 |
| WO | 2010103344 A1 | 9/2010 |

(56) References Cited

FOREIGN PATENT DOCUMENTS

| | | |
|---|---|---|
| WO | 2012031267 A1 | 3/2012 |
| WO | 2015009793 A1 | 1/2015 |

* cited by examiner

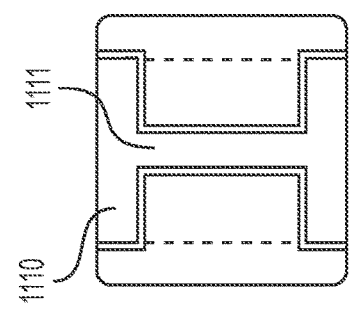
FIG. 32B
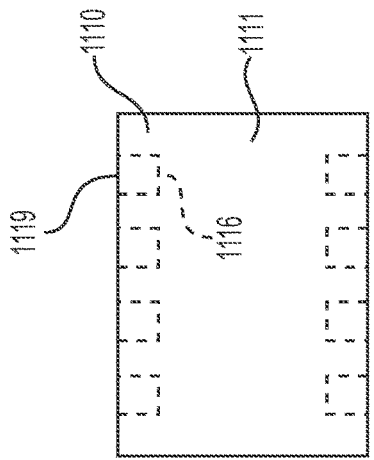
FIG. 32D
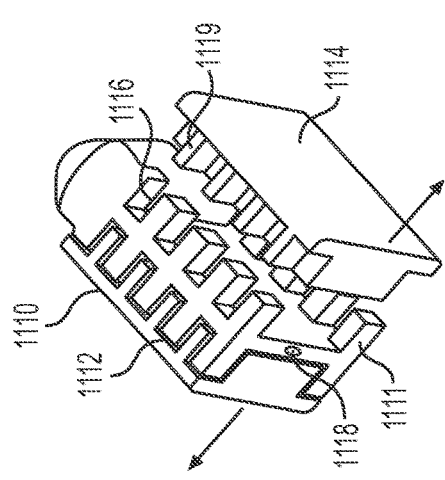
FIG. 32A
FIG. 32C

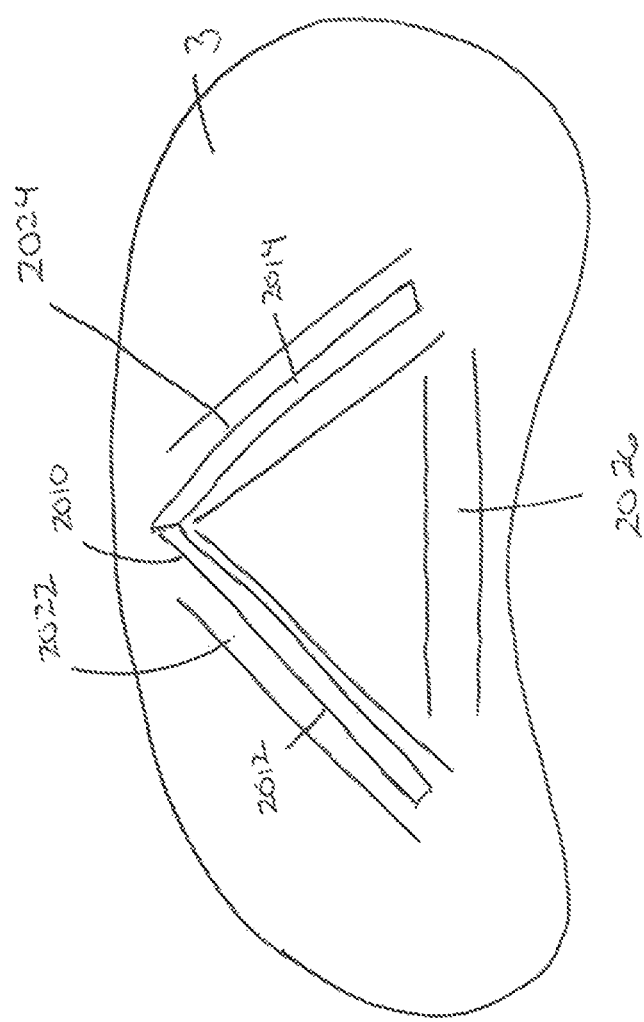

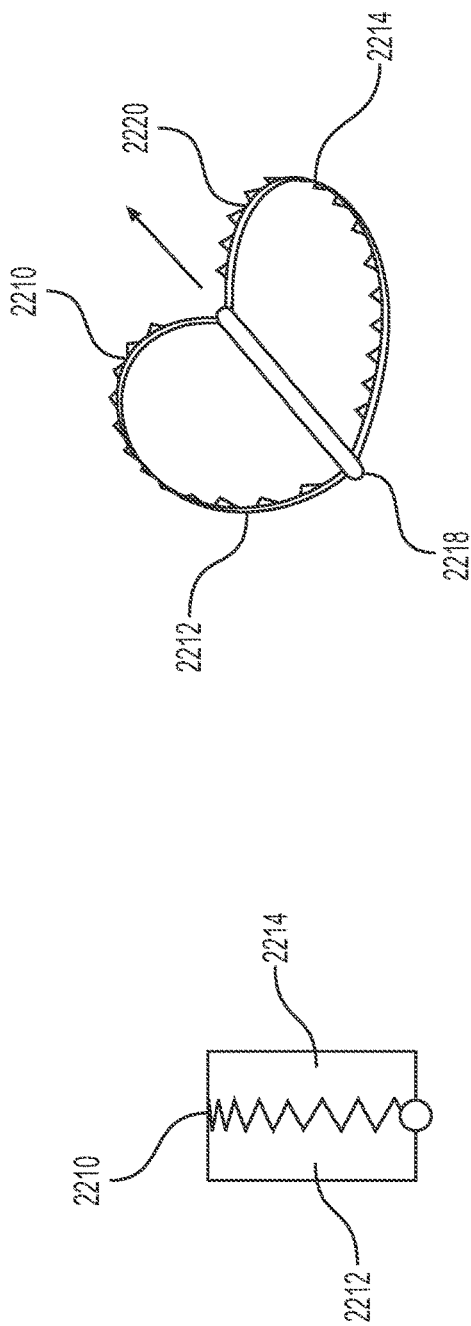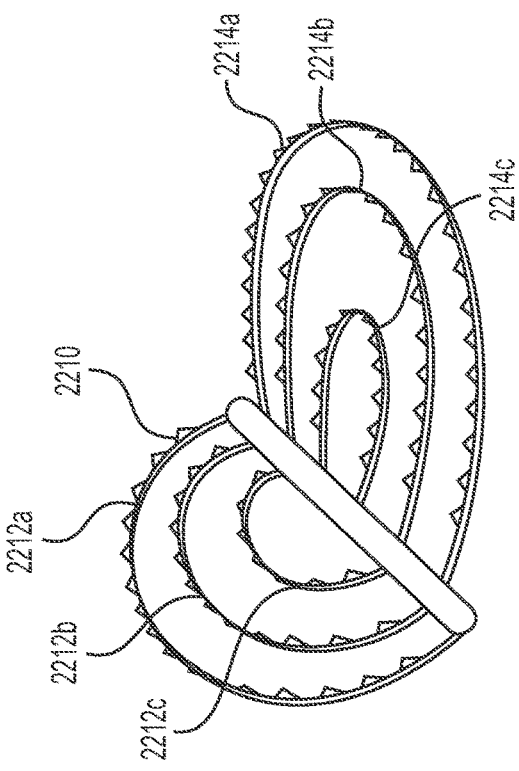

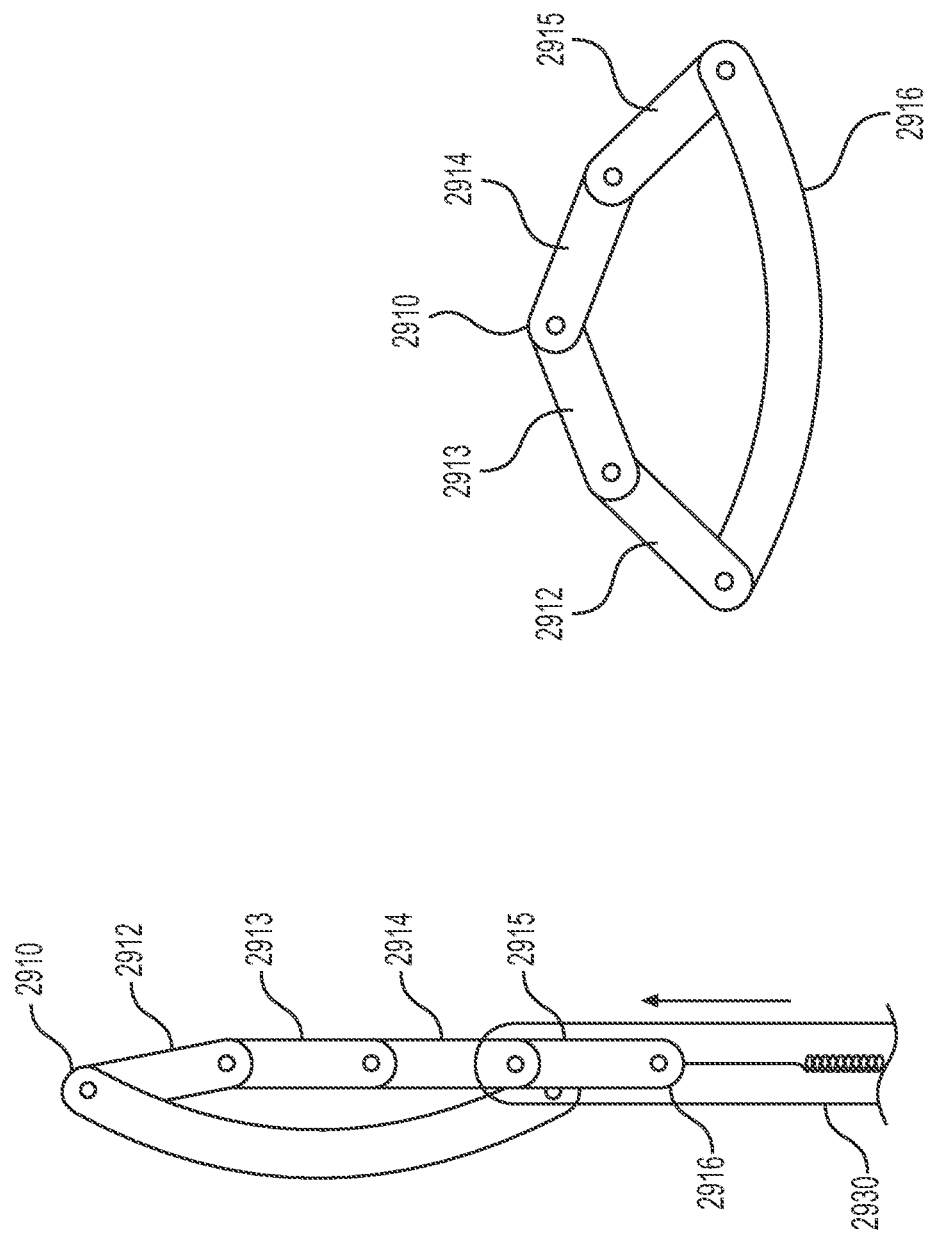

EXPANDABLE INTERBODY SPACER

CROSS REFERENCE TO RELATED APPLICATIONS

This patent application is a continuation of U.S. patent application Ser. No. 16/660,174 filed on Oct. 22, 2019 which is a continuation of U.S. patent application Ser. No. 15/264,677, filed Sep. 14, 2016, which is a continuation of U.S. patent application Ser. No. 13/941,095, filed Jul. 12, 2013, which is a continuation-in-part application of U.S. patent application Ser. No. 13/483,852, filed May 30, 2012, now U.S. Pat. No. 9,044,342, which are incorporated by reference herein in their entireties for all purposes.

FIELD OF THE INVENTION

The present invention relates to devices and methods for treating one or more damaged, diseased, or traumatized portions of the spine, including intervertebral discs, to reduce or eliminate associated back pain. In one or more embodiments, the present invention relates to an expandable interbody spacer.

BACKGROUND OF THE INVENTION

The vertebrate spine is the axis of the skeleton providing structural support for the other body parts. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The centers of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the annulus fibrosus ("annulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc.

The spinal disc and/or vertebral bodies may be displaced or damaged due to trauma, disease, degenerative defects, or wear over an extended period of time. One result of this displacement or damage to a spinal disc or vertebral body may be chronic back pain. A common procedure for treating damage or disease of the spinal disc or vertebral body may involve partial or complete removal of an intervertebral disc. An implant, which may be referred to as an interbody spacer, can be inserted into the cavity created where the intervertebral disc was removed to help maintain height of the spine and/or restore stability to the spine. An example of an interbody spacer that has been commonly used is a cage, which typically is packed with bone and/or bone-growth-inducing materials. However, there are drawbacks associated with conventional interbody spacers, such as cages and other designs. For instances, conventional interbody spacers may be too large and bulky for introduction into the disc space in a minimally invasive manner, such as may be utilized in a posterior approach. Further, these conventional interbody spacers may have inadequate surface area contact with the adjacent endplates if sized for introduction into the disc space in a minimally invasive manner. In addition, conventional interbody spacers designed for introduction into the disc space in a minimally invasive manner may lack sufficient space for packing of bone-growth-inducing material, thus potentially not promoting the desired graft between the adjacent endplates.

Therefore, a need exists for an interbody spacer that can be introduced in a minimally manner that provides a desired amount of surface area contact with the adjacent endplates and has an increased space for packing of bone-growth-inducing material.

SUMMARY OF THE INVENTION

The present invention relates to an expandable interbody spacer. The expandable interbody spacer may comprise a first jointed arm comprising a plurality of links pivotally coupled end to end. The expandable interbody spacer further may comprise a second jointed arm comprising a plurality of links pivotally coupled end to end. The first jointed arm and the second jointed arm may be interconnected at a proximal end of the expandable interbody spacer. The first jointed arm and the second jointed arm may be interconnected at a distal end of the expandable interbody spacer. The first jointed arm and the second jointed arm may each be configured to fold inward in opposite directions to place the expandable interbody spacer in an expanded position.

BRIEF DESCRIPTION OF THE DRAWINGS

The present invention will be more readily understood with reference to the embodiments thereof illustrated in the attached drawing figures, in which:

FIGS. 32A-32D show an expandable spacer comprising an "I-beam" with multiple side slots for receiving complementary side members in accordance with embodiments of the present invention;

FIG. 41 shows a buildable spacer that can be guided by tracks in a disc space to form a large footprint in a disc space in accordance with some embodiments;

FIGS. 43A-C show an expandable spacer capable of outward folding in accordance with some embodiments;

FIGS. 49A and 49B show an expandable spacer having asymmetrical expansion in accordance with some embodiments.

Throughout the drawing figures, it should be understood that like numerals refer to like features and structures.

DETAILED DESCRIPTION OF THE INVENTION

Figure 1:
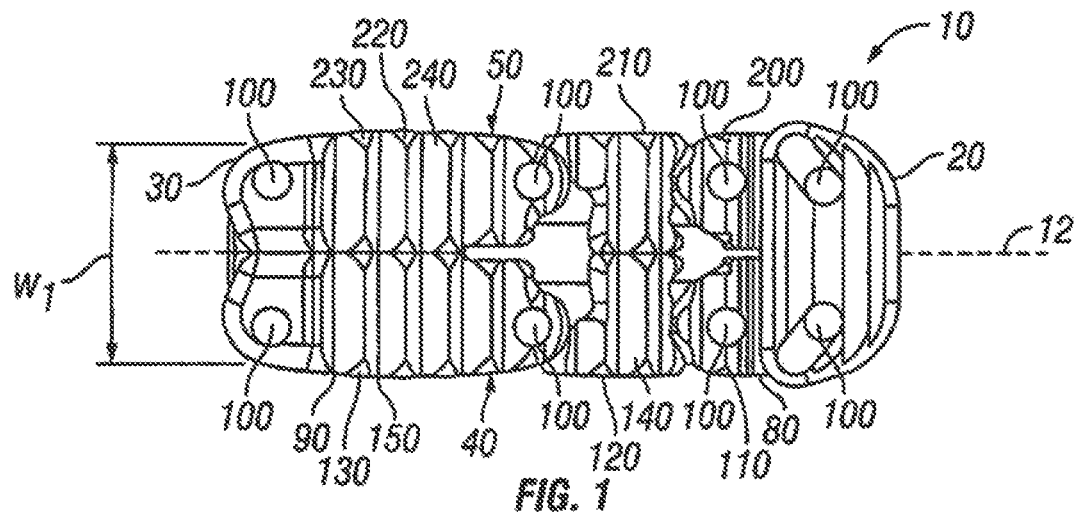
FIG. 1 is a top view of an expandable interbody spacer shown in a collapsed position in accordance with embodiments of the present invention.
Figure 2:
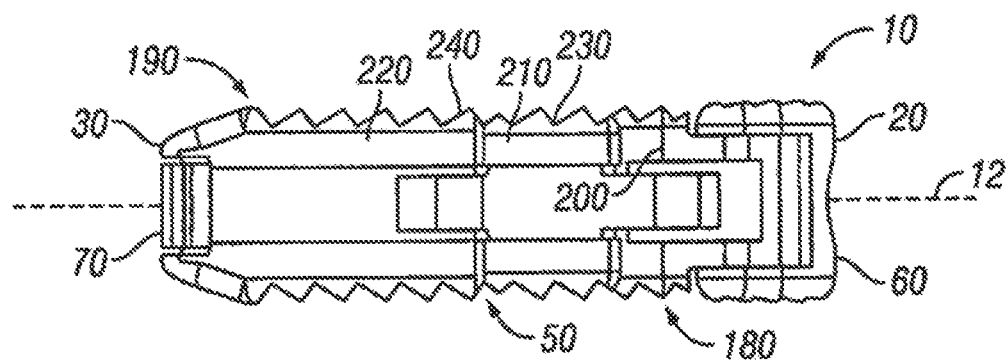
FIG. 2 is a side view of the expandable interbody spacer of FIG. 1 shown in a collapsed position.

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Referring to FIGS. 1-10, an expandable interbody spacer 10 is shown in accordance with embodiments of the present invention. In the illustrated embodiment, the expandable interbody spacer 10 has a proximal end 20 and a distal end 30. The expandable interbody spacer 10 may include a first jointed arm 40 and a second jointed arm 50 positioned on either side of longitudinal axis 15 of the spacer 10. The first and second jointed arms 40, 50 may be interconnected at the proximal end 20, for example, by a proximal connection member 60. The first and second jointed arms 40, 50 may be interconnected at the distal end 30, for example, by a distal connection member 70. The first and second jointed arms 40, 50 The expandable interbody spacer 10 may be made from a number of materials, including titanium, stainless steel, titanium alloys, non-titanium alloys, polymeric materials, plastic composites, polyether ether ketone ("PEEK") plastic material, ceramic, elastic materials, and combinations thereof. While the expandable interbody spacer 10 may be used with a posterior, anterior, lateral, or combined approach to the surgical site, the spacer 10 may be particularly suited with a posterior approach.

The first jointed arm 40 has a proximal end 80 and a distal end 90. The proximal end 80 may be pivotally coupled to the proximal connection member 60. The distal end 90 may be pivotally coupled to the distal connection member 70. Any of a variety of different fasteners may be used to pivotally couple the proximal end 80 and the distal end 90 and the proximal connection member 60 and the distal connection member 70, such as pins 100, for example. In another embodiment (not illustrated), the connection may be a hinged connection. As illustrated, the first jointed arm 40 may comprise a plurality of links that are pivotally coupled to one another. In the illustrated embodiment, the first jointed arm 40 comprises first link 110, second link 120, and third link 130. When the spacer 10 is in a collapsed position, the first link 110, second link 120, and third link may be generally axially aligned. As illustrated, the first link 110, second link 120, and third link 130 may be connected end to end. When the spacer 10 is in a collapsed position, the first link 110, second link 120, and third link 130 may be generally axially aligned. The first link 110 and the second link 120 may be pivotally coupled, and the second link 120 and the third link 130 may also be rotatably coupled. Any of a variety of different fasteners may be used to pivotally couple the links 110, 120, 130, such as pins 100, for example. In another embodiment (not illustrated), the coupling may be via a hinged connection.

As best seen in FIGS. 1, 5-7, 9, and 10, an upper surface 140 of the first jointed arm 40 may be defined by the links 110, 120, 130. The upper surface 140 should allow for engagement of the first jointed arm 40 with one of the adjacent vertebral bodies. In some embodiments, the upper surface 140 may include texturing 150 to aid in gripping the adjacent vertebral bodies. Although not limited to the following, the texturing 150 can include teeth, ridges, friction-increasing elements, keels, or gripping or purchasing projections.

Figure 7:
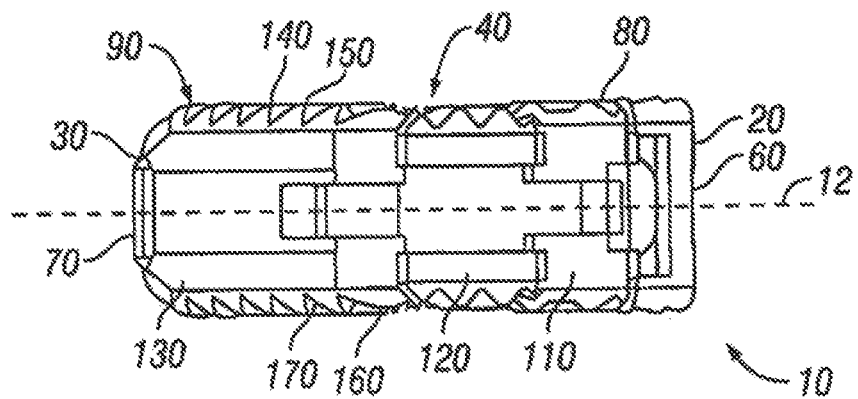
FIG. 7 is a right side view of the expandable interbody spacer of FIG. 1 shown in an expanded position.
Figures 9, 10:
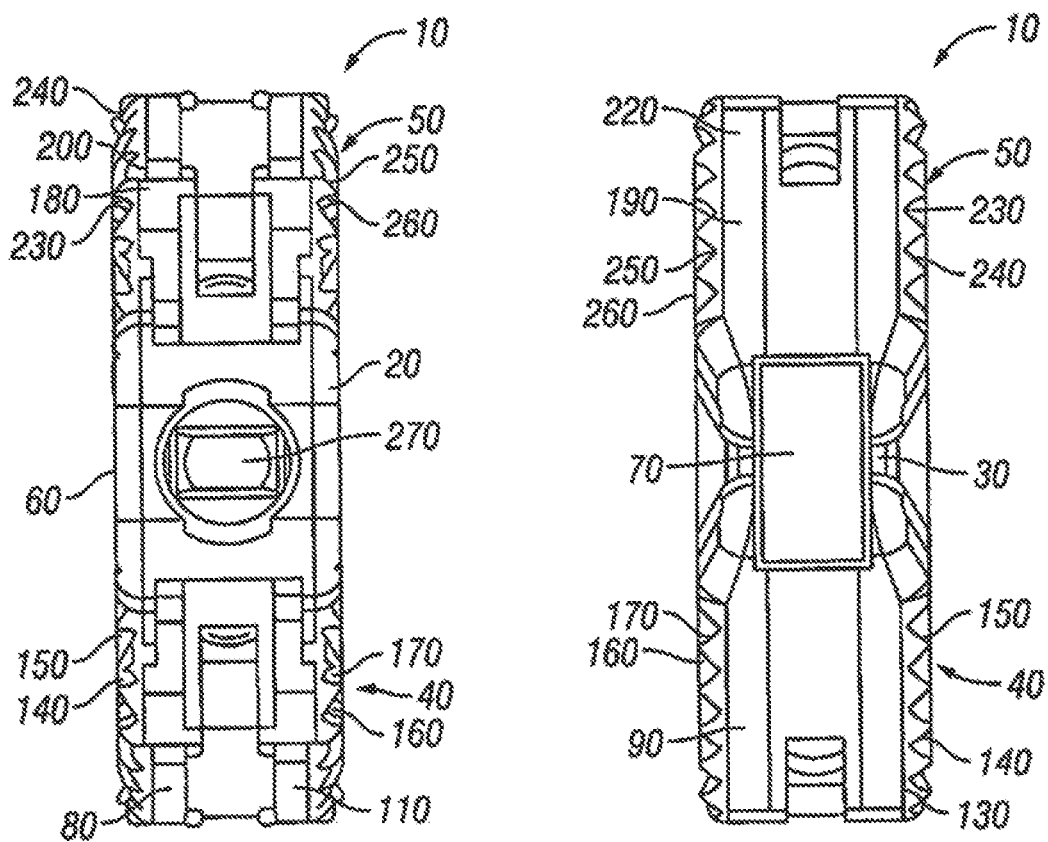
FIG. 9 is a proximal end view of the expandable interbody spacer of FIG. 1 shown in an expanded position.
FIG. 10 is a distal end view of the expandable interbody spacer of FIG. 1 shown in an expanded position.

As best seen in FIGS. 7, 9, and 10 a lower surface 160 of the first jointed arm 40 may be defined by the links 110, 120, 130. The lower surface 160 should allow for engagement of the first jointed arm 40 with one of the adjacent vertebral bodies. In some embodiments, the lower surface 160 may include texturing 170 to aid in gripping the adjacent vertebral bodies. Although not limited to the following, the texturing 170 can include teeth, ridges, friction-increasing elements, keels, or gripping or purchasing projections.

The second jointed arm 50 has a proximal end 180 and a distal end 190. The proximal end 180 may be pivotally coupled to the distal connection member 70. The distal end 190 may be pivotally coupled to the distal connection member 70. Any of a variety of different fasteners may be used to pivotally couple the proximal end 180 and the distal end 190 and the proximal connection member 60 and the distal connection member 70, such as pins 100, for example. In another embodiment (not illustrated), the connection may be a hinged connection. As illustrated, the second jointed arm 50 may comprise a plurality of links that are pivotally coupled to one another. In the illustrated embodiment, the second jointed arm 50 comprises first link 200, second link 210, and third link 220. When the spacer 10 is in a collapsed position, the first link 200, second link 210, and third link 220 may be generally axially aligned. As illustrated, the first link 200, second link 210, and third link 220 may be connected end to end. The first link 200 and the second link 210 may be pivotally coupled, and the second link 210 and the third link 220 may also be pivotally coupled. Any of a variety of different fasteners may be used to pivotally couple the links 200, 210, 220, such as pins 100, for example. In another embodiment (not illustrated), the coupling may be via a hinged connection.

As best seen in FIGS. 1, 2, 6, and 8-10, an upper surface 230 of the second jointed arm 50 may be defined by the links 200, 210, 220. The upper surface 230 should allow for engagement of the second jointed arm 50 with one of the adjacent vertebral bodies. In some embodiments, the upper surface 230 may include texturing 240 to aid in gripping the adjacent vertebral bodies. Although not limited to the following, the texturing 240 can include teeth, ridges, friction-increasing elements, keels, or gripping or purchasing projections.

Figure 8:
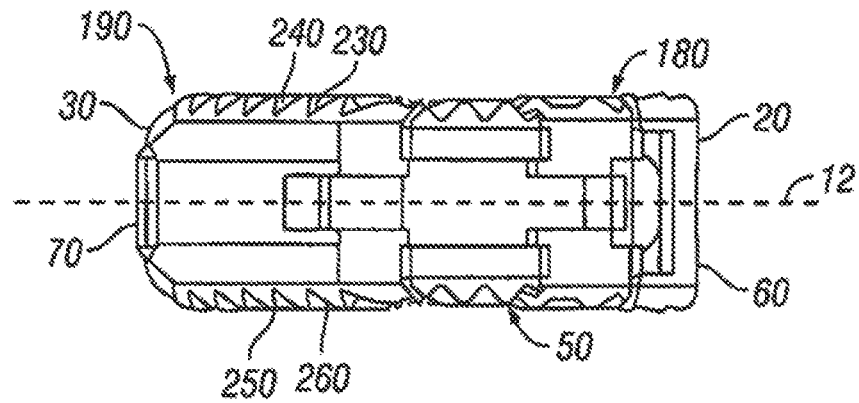
FIG. 8 is a left side view of the expandable interbody spacer of FIG. 1 shown in an expanded position.

As best seen in FIGS. 8-10, a lower surface 250 of the second jointed arm 50 may be defined by the links 200, 210, and 220. The lower surface 250 should allow for engagement of the second jointed arm 50 with one of the adjacent vertebral bodies. In some embodiments, the lower surface 250 may include texturing 260 to aid in gripping the adjacent vertebral bodies. Although not limited to the following, the texturing 260 can include teeth, ridges, friction-increasing elements, keels, or gripping or purchasing projections.

Figure 3:
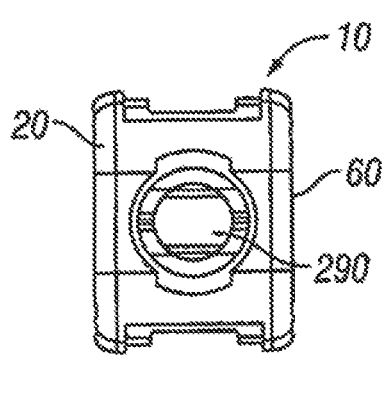
FIG. 3 is a proximal end view of the expandable interbody spacer of FIG. 1 shown in a collapsed position.
Figure 4:
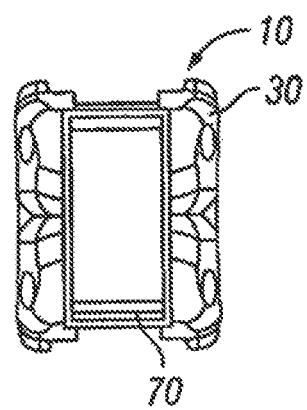
FIG. 4 is a distal end view of the expandable interbody spacer of FIG. 1 shown in a collapsed position.
Figure 5:
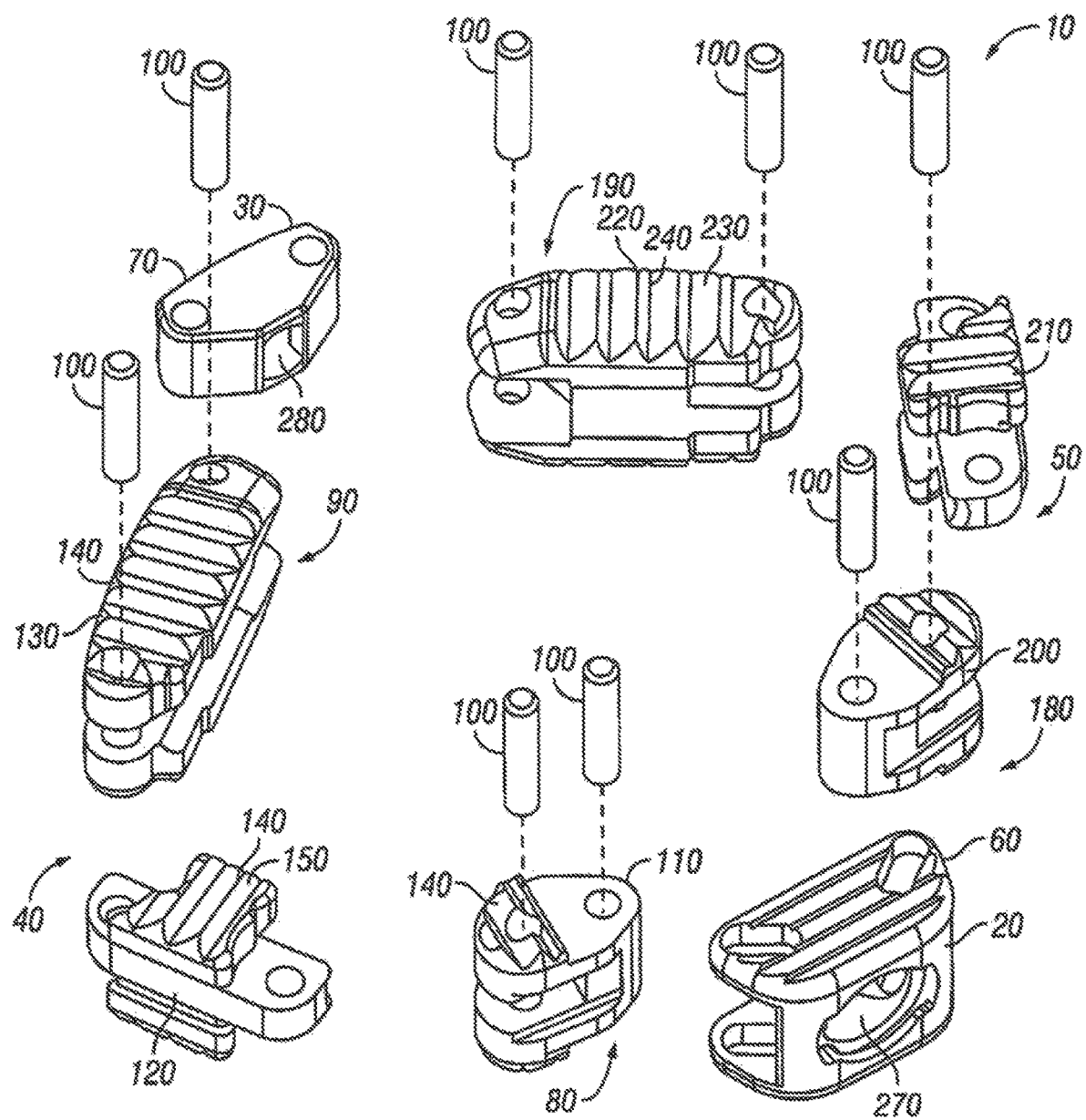
FIG. 5 is an exploded view of the expandable interbody spacer of FIG. 1.

With reference now to FIGS. 3, 5, and 9, a bore 270 extends through proximal connection end 60. The bore 270 may extend generally parallel to the longitudinal axis 12 (see FIG. 1) of the spacer 10. The first jointed arm 40 and the second jointed arm 50 may define a hollow interior portion (not shown) that extends axially through the spacer 10. The bore 270 in the proximal connection end 60 may communicate with this hollow interior portion. As best shown on FIG. 5, the distal connection end 70 may include an opening 280. As illustrated, the opening 280 may face inward and may not extend all the way through the distal connection 70. In one embodiment, the opening 280 may be generally aligned with the bore 270 in the proximal connection end 60 such at a tool (e.g., tool 340 shown on FIG. 12) inserted into the bore 270 may be received in the opening 280 for placement of the spacer 10 into a disc space and/or expansion of the spacer 10.

FIGS. 1-4 illustrate the expandable interbody spacer 10 in a collapsed position. In accordance with present embodiments, the expandable interbody spacer 10 may be laterally expanded to an expanded position. FIGS. 6-10 illustrate the expandable interbody spacer 10 in an expanded position. In the expanded position, the first arm 40 and the second arm 50 have each been folded inward in opposite directions. For example, the proximal end 80 and the distal end 90 of the first arm 40 may be folded closer together. The links 110, 120, 130 should pivot with respect to one another when the first arm 40 is folded inward. The proximal end 80 should pivot at the proximal connection end 60, and the distal end 90 should pivot at the distal connection end 70. By way of further example, the proximal end 180 and the distal end 190 of the second arm 50 may also be folded together. The links 200, 210, 220 should pivot with respect to another when the second arm is folded inward. The proximal end 180 should pivot at proximal connection end 60, and the distal end 190 should pivot at the distal connection end 70. After placement in the expanded position, the expandable interbody spacer 10 can be secured in the expanded position to prevent collapse of the expandable interbody spacer 10 upon application of spacer. Any of a variety of different techniques may be used to secure the expandable interbody spacer 10, including pins or other suitable locking mechanism, for example.

Figure 6:
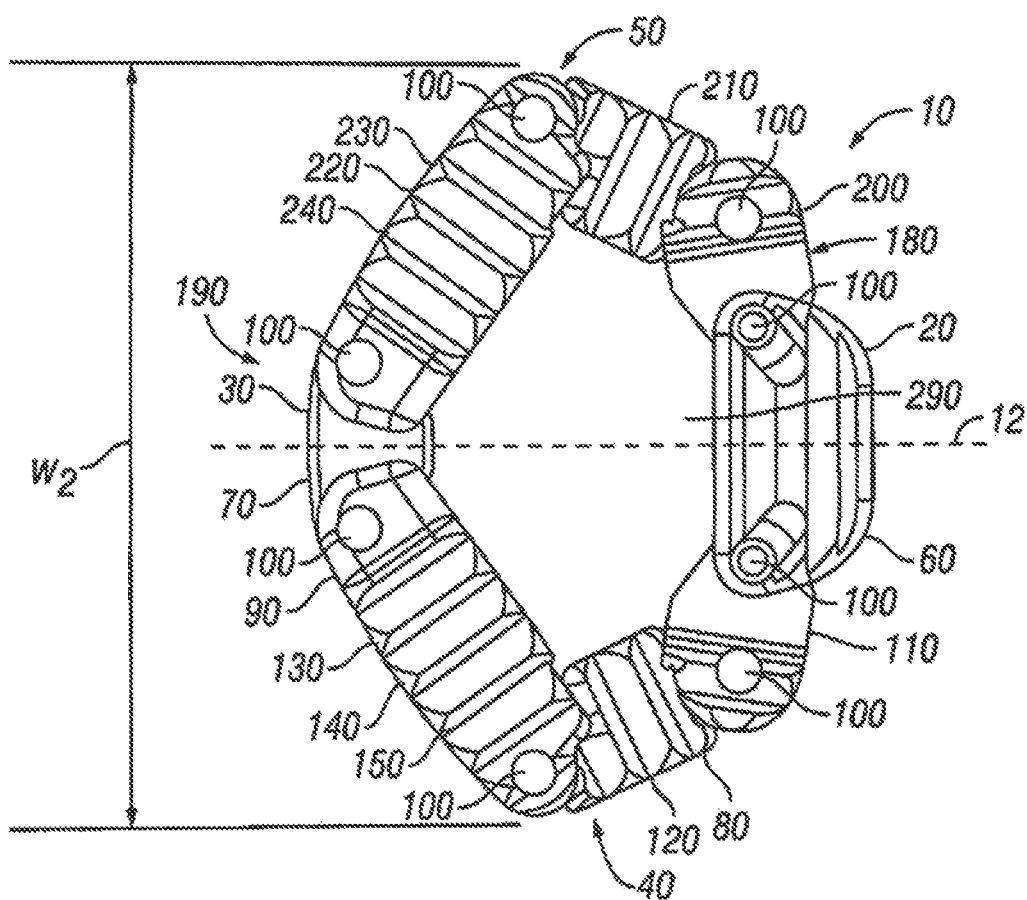
FIG. 6 is a top view of the expandable interbody spacer of FIG. 1 shown in an expanded position.

As illustrated by FIG. 6, the first and second jointed arms 40, 50 define an interior cavity 290 when in an expanded position. The interior cavity 290 may be filled with a bone-growth-inducing material, such as bone material, bone-growth factors, or bone morphogenic proteins. As will be appreciated by those of ordinary skill in the art, the bone-growth-inducing material should induce the growth of bone material, thus promoting fusion of the adjacent vertebra.

The expandable interbody spacer 10 may be sized to accommodate different applications, different procedures, implantation into different regions of the spine, or size of disc space. For example, the expandable interbody spacer 10 may have a width W1 (as shown on FIG. 1) prior to expansion of about 8 to about 22 and alternatively from about 10 to about 13. By way of further example, the expandable interbody spacer 10 may be expanded to a width W2 (as shown on FIG. 6) in a range of about 26 to about 42 and alternatively from about 16 to about 32. It should be understood that the width W1 or W2 whether prior to, or after, expansion generally refers to the width of the expandable interbody spacer 10 extending transverse to the longitudinal axis 12 of the spacer 10. In general, the width W2 of the expandable interbody spacer 10 after expansion should be greater than the width W1 of the expandable interbody spacer 10 prior to expansion.

Figure 11:
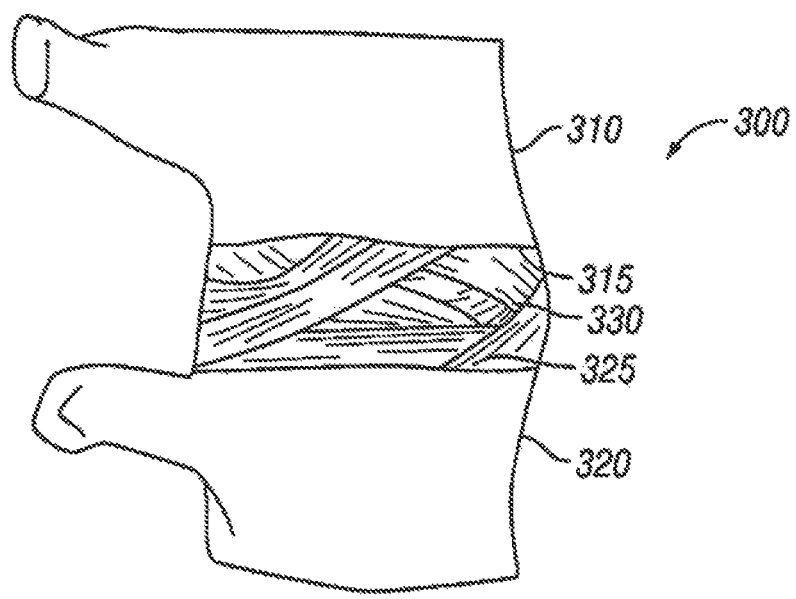
FIG. 11 is a view showing disc space between adjacent vertebrae in accordance with embodiments of the present invention.
Figure 12:
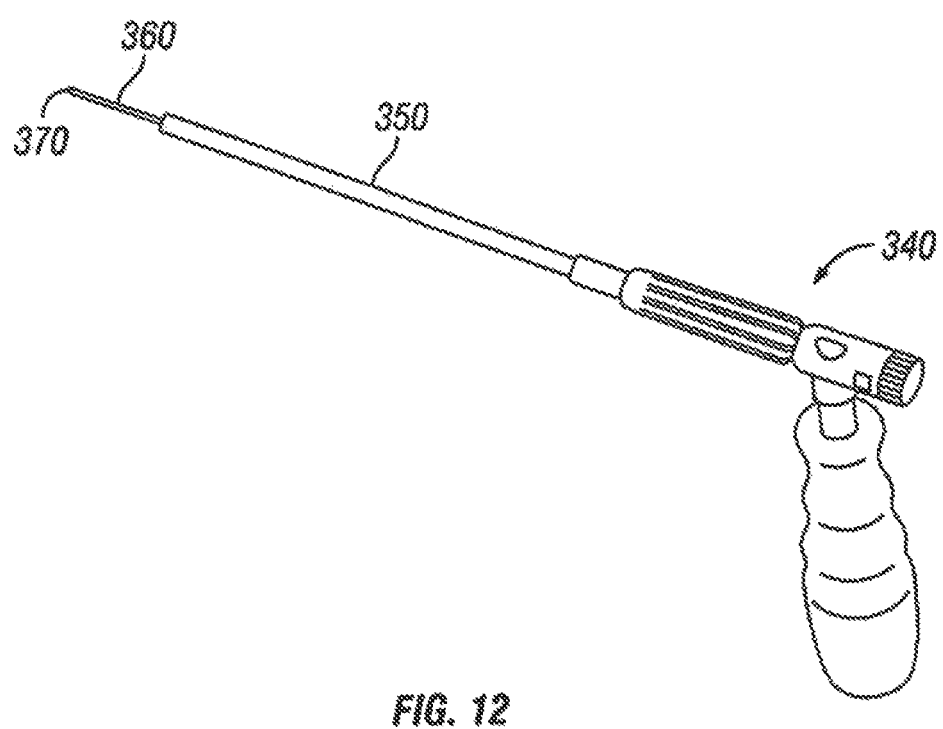
FIG. 12 is a view of a tool for insertion of an expandable interbody spacer in accordance with embodiments of the present invention.

In accordance with present embodiments, the expandable interbody spacer 10 may be used in the treatment of damage or disease of the vertebral column. In one embodiment, the expandable interbody spacer 10 may be inserted into a disc space between adjacent vertebrae in which the intervertebral disc has been partially or completely removed. FIG. 11 illustrates a spinal segment 300 into which the expandable interbody spacer 10 (e.g., FIGS. 1-10) may be inserted. The spinal segment 300 includes adjacent vertebrae, identified by reference numbers 310 and 320. Each of the adjacent vertebrae 310, 320 has a corresponding endplate 315, 325. The disc space 330 is the space between the adjacent vertebrae 310, 320. FIG. 12 illustrates a tool 340 that may be used in the insertion of the expandable interbody spacer 10 into the disc space 330. The tool 340 includes a shaft 350 having an elongated end portion 360 for coupling to the expandable interbody spacer 10. The elongated end portion 360 has a distal tip 370.

Figure 13:
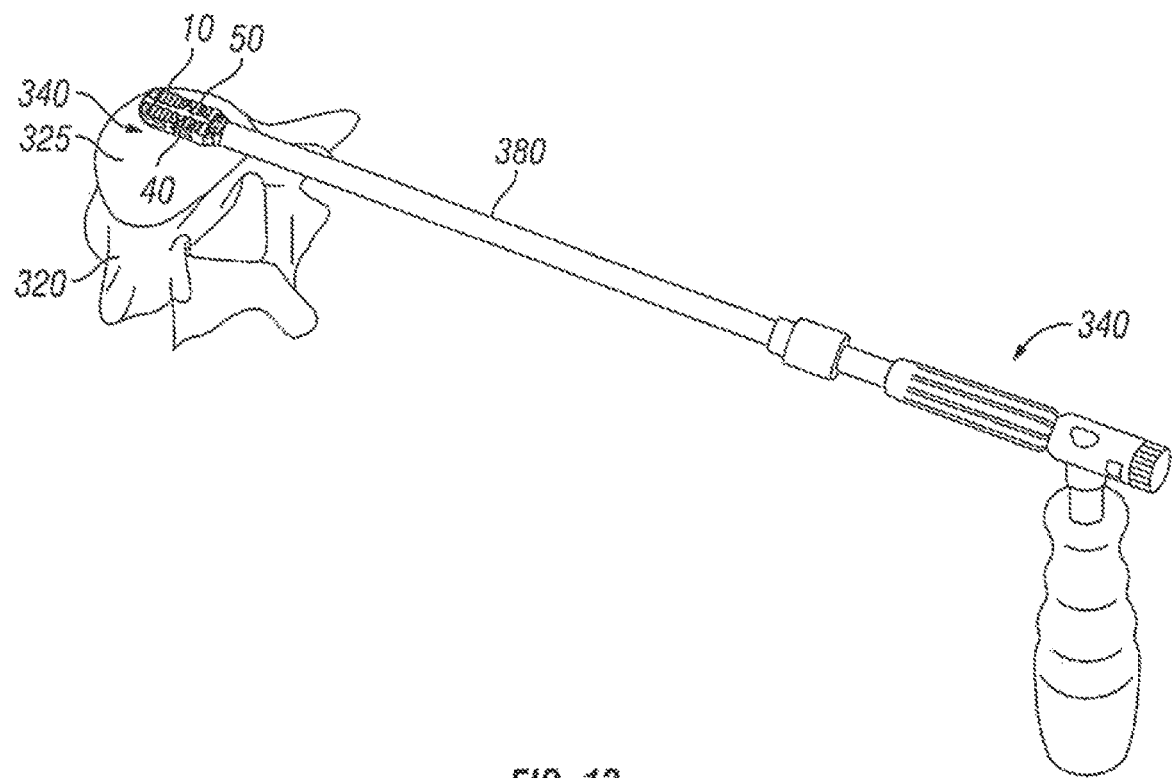
FIG. 13 is a view showing the tool of FIG. 12 introducing an expandable interbody spacer into a disc space in a collapsed position in accordance with embodiments of the present invention.
Figure 14:
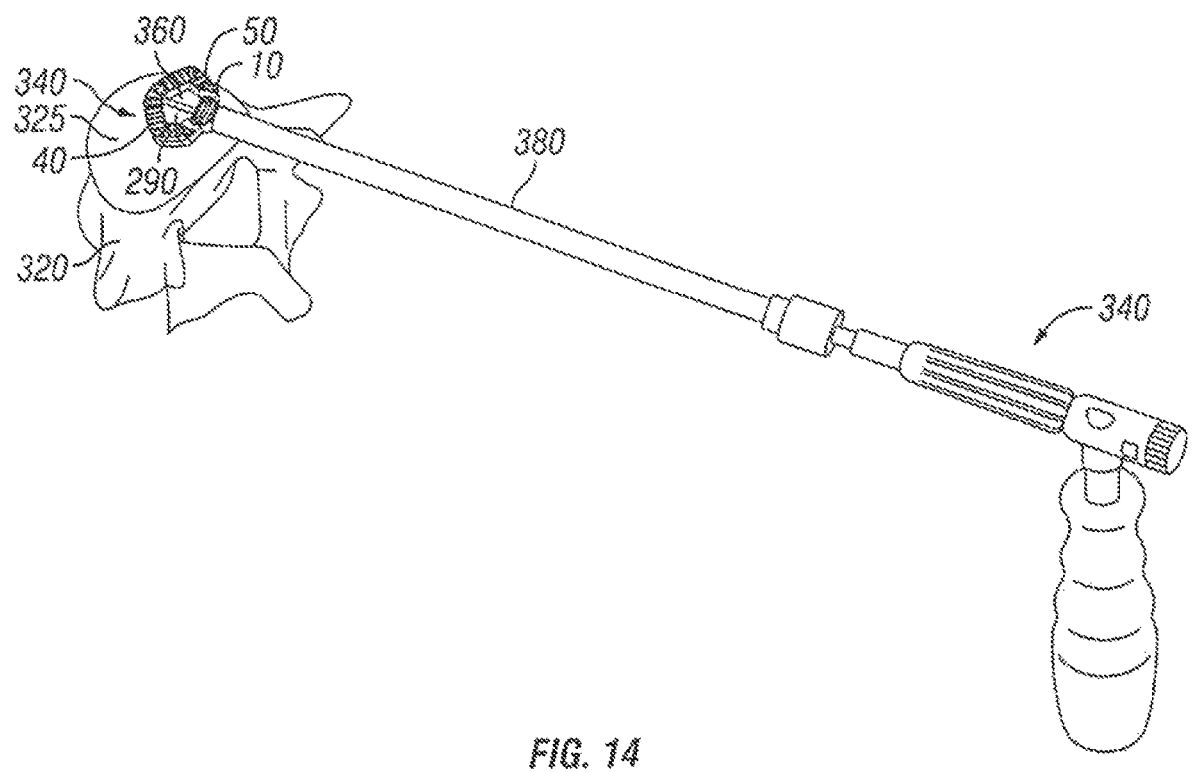
FIG. 14 is a view showing the tool of FIG. 12 expanding an expandable interbody spacer in a disc space in accordance with embodiments of the present invention.
Figure 15:
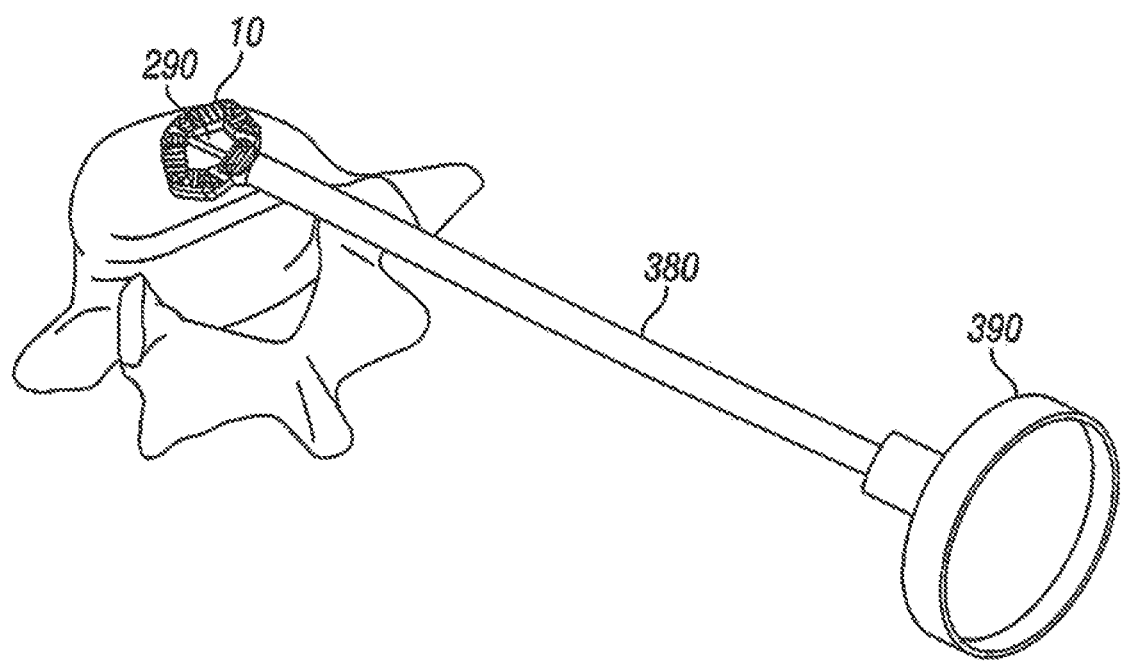
FIG. 15 is a view showing a funnel for introduction of bone-growth-inducing material into a disc space in accordance with embodiments of the present invention.

FIGS. 13 and 14 illustrate introduction of an expandable interbody spacer 10 into the disc space 330 using tool 340. For illustrative purposes, the upper vertebra 330 shown on FIG. 11 has been removed from FIGS. 13 and 14. As illustrated, the spacer 10 may be secured to the tool 340. For example, the elongated end portion 360 of the tool 340 may be disposed through the bore 270 (e.g., see FIG. 5) in the proximal connection end 60 with the distal tip 370 (e.g., see FIG. 12) of the end portion 360 secured in the opening 280 (e.g., see FIG. 5) in the distal connection end 70. As illustrated by FIG. 13, the tool 340 may introduce the spacer 10 into the disc space 330 through an access cannula 380. After introduction into the disc space 330, the spacer 10 may be laterally expanded. In accordance with present embodiments, the spacer 10 can be laterally expanded by folding the first arm 40 and the second arm 50 inward. By expanding laterally, the spacer 10 has an increased surface area contact with the endplate 325. In addition, the spacer 10 may engage harder bone around the apophyseal ring. As previously mentioned, an interior cavity 290 should be formed in the spacer 10 when in the expanded position. The tool 340 may then be detached from the spacer 10 and removed from the cannula 380. As illustrated by FIG. 15, a funnel 390 may then be placed on the cannula 380. Bone-growth inducing material may then be placed into the interior cavity 290 through the cannula 380. Because the spacer 10 has been laterally expanded, the interior cavity 290 should have a desirable amount of space for packing of the bone-growth-inducing material.

Figure 16:
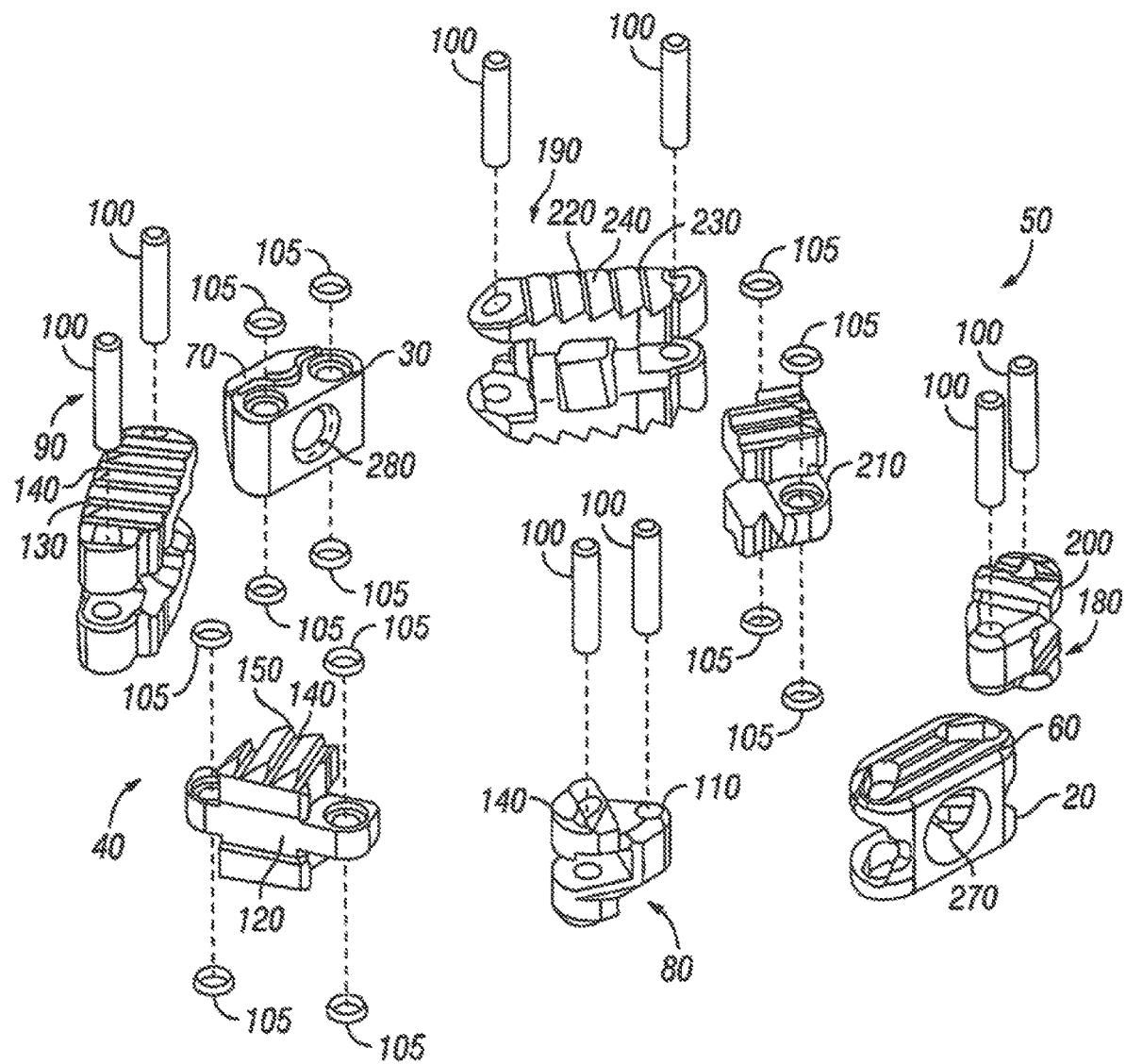
FIG. 16 is an exploded view of another embodiment of an expandable interbody spacer.

FIG. 16 illustrates an expandable interbody spacer 10 in accordance with an alternative embodiment. In the illustrated embodiment, the expandable interbody spacer 10 comprises a first jointed arm 40 and a second jointed arm 50. The first jointed arm 40 has a proximal end 80 and a distal end 90. The first jointed arm 40 comprises a plurality of links 110, 120, 130 connected end to end, for example, by pins 100. The first jointed arm 40 further may comprise washers 105 (e.g., PEEK washers) that may be disposed between the links 110, 120, 130 at their connections. The second jointed arm 50 has a proximal end 180 and a distal end 190. The second jointed arm 50 comprises a plurality of links 200, 210, 220 connected end to end, for example, by pins 100. The second jointed arm 50 further may comprise washers 105 (e.g., PEEK washers) that may be disposed between the links 200, 210, 220 at their connections. Washers 105 may also be disposed between the first arm 40 and the proximal connection member 60 and the distal connection member 70 at their respective connections. Washers 105 may also be disposed between the second arm 50 and the proximal connection member 60 and the distal connection member 70 at their respective connections. The washers 105 should have an interference fit to cause friction such that the spacer 10 may hold its shape in the entire range of the expanded implant.

Figure 19:
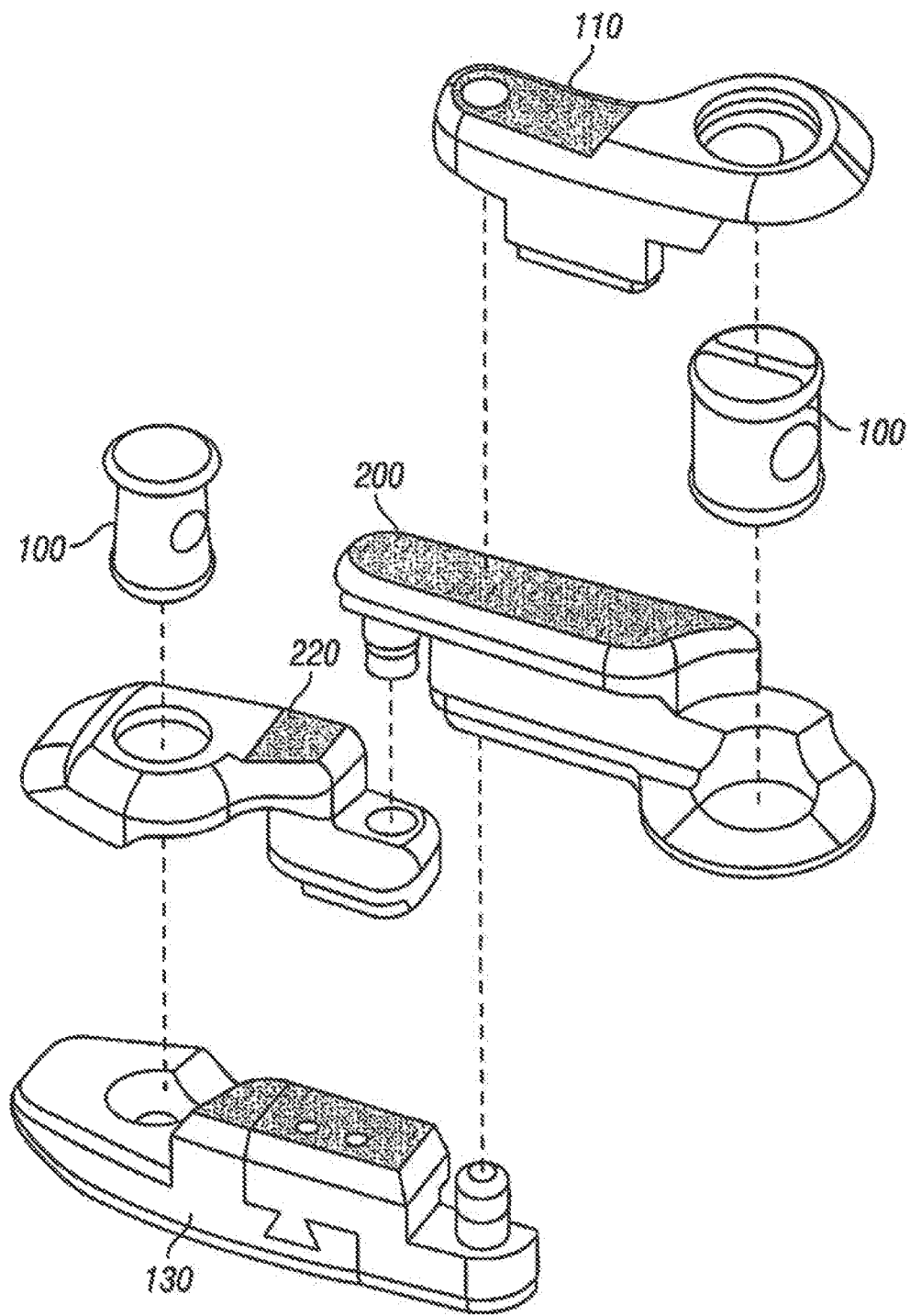
FIG. 19 is an exploded view of the expandable interbody spacer of FIG. 17.

The proximal ends 80, 180 may be pivotally coupled, for example, by pin 100, as shown on FIG. 19. The distal ends 90, 180 may also be pivotally coupled, for example, by pin 100, as shown on FIG. 19. The first jointed arm 40 comprises first link 110 and third link 130, the first link 110 and the third link 130 being pivotally coupled. In contrast to the first jointed arm 40 of FIGS. 1-10, there is no second link 120.

Figure 17:
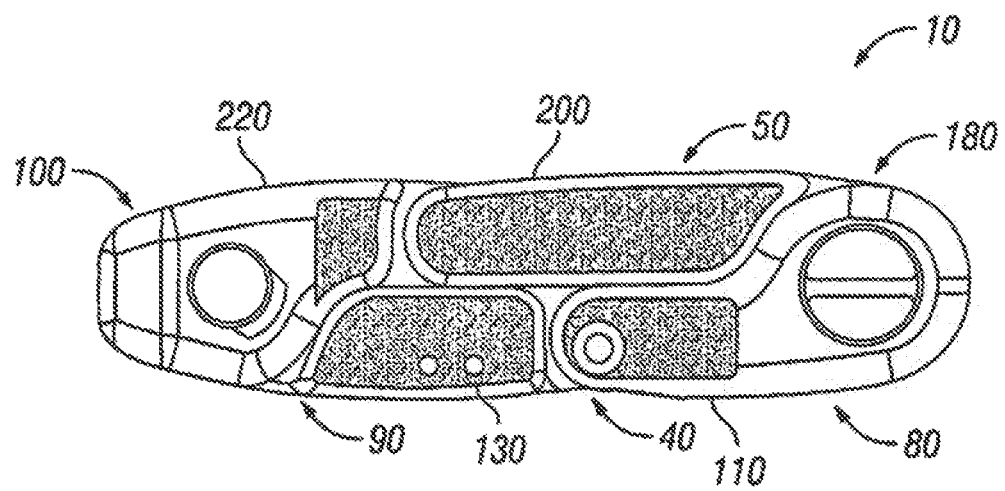
FIG. 17 is a top view of another embodiment of an expandable interbody spacer shown in a collapsed position.
Figure 18:
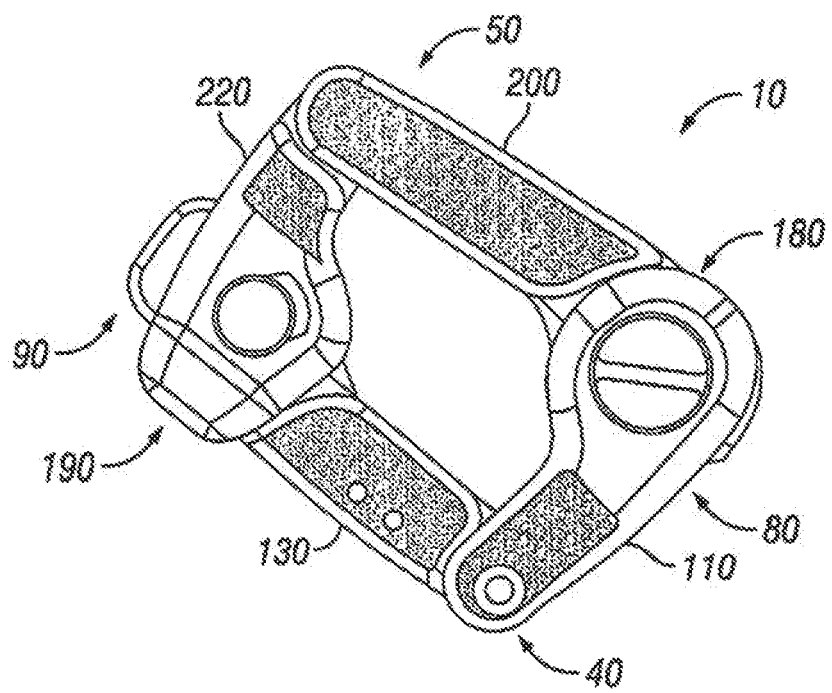
FIG. 18 is a top view of the expandable interbody spacer of FIG. 17 shown in an expanded position.
Figure 20:
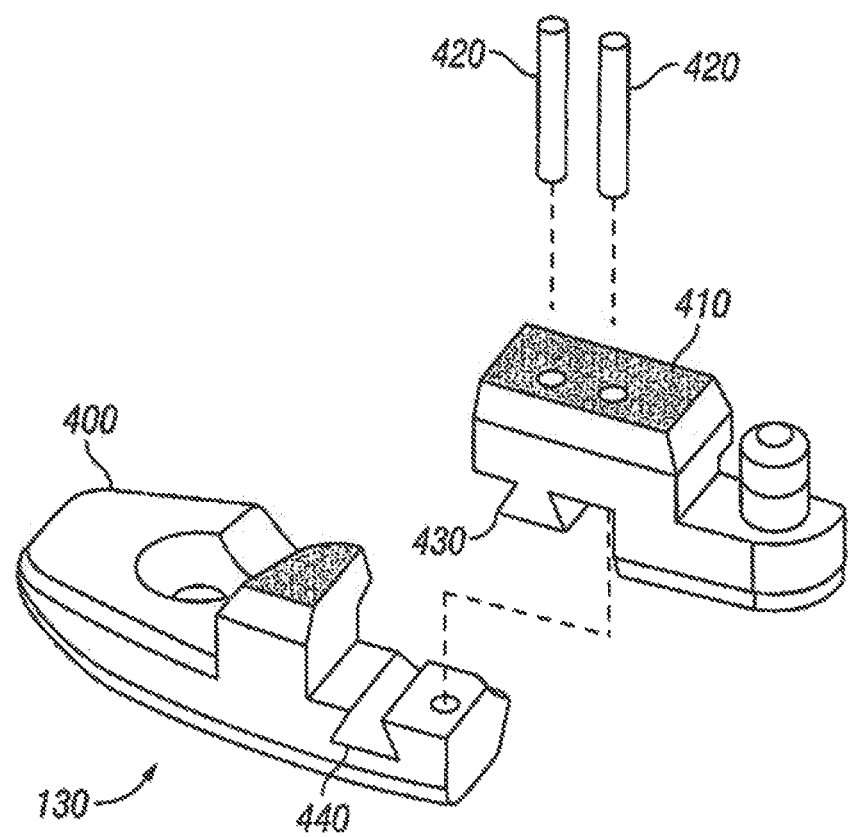
FIG. 20 is an exploded view of a link of a jointed arm of the expandable interbody spacer of FIG. 17.

Referring now to FIGS. 17-19, an expandable interbody spacer 10 is illustrated in accordance with another embodiment of the present invention. In the illustrated embodiment, the expandable interbody spacer 10 comprises a first jointed arm 40 and a second jointed arm 50. The first jointed arm 40 has a proximal end 80 and a distal end 90. The second jointed arm 50 has a proximal end 180 and a distal end 190. The proximal ends 80, 180 may be pivotally coupled, for example, by pin 100, as shown on FIG. 19. The distal ends 90, 180 may also be pivotally coupled, for example, by pin 100, as shown on FIG. 19. The first j ointed arm 40 comprises first link 110 and third link 130, the first link 110 and the third link 130 being pivotally coupled. In contrast to the first jointed arm 40 of FIGS. 1-10, there is no second link 120. As shown by FIG. 20, the third link 130 may comprise a first link segment 400 and a second link segment 410, which may be secured to one another by pins 420, for example. First link segment 400 and second link segment 410 may also have a tongue-and-groove connection, for example a groove 430 in the first link segment 400 may receive a tongue 440 of the second link segment 410. The second jointed arm comprises first link 200 and third link 220, the first link 200 and the third link 220 being pivotally coupled. In contrast to the second joint arm 50 of FIGS. 1-10, there is no second link 210.

In accordance with present embodiments, lateral expansion of the expandable interbody spacer 10 of FIGS. 17-19 may include folding the first arm 40 and the second arm 50 inward. For example, the proximal end 80 and the distal end 90 of the first arm 40 may be folded together, and the proximal end 180 and the distal end 190 of the second arm 50 may also be folded together.

Figure 21:
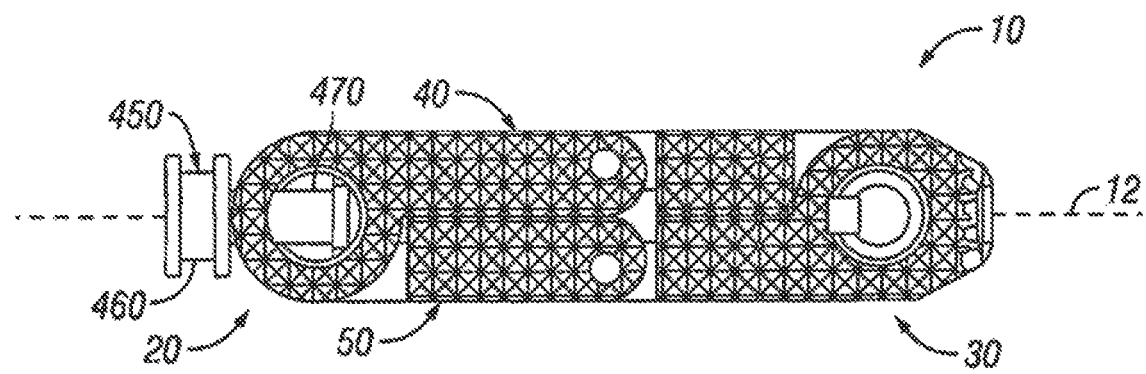
FIG. 21 is a top view of another embodiment of an expandable interbody spacer shown in a collapsed position.
Figure 22:
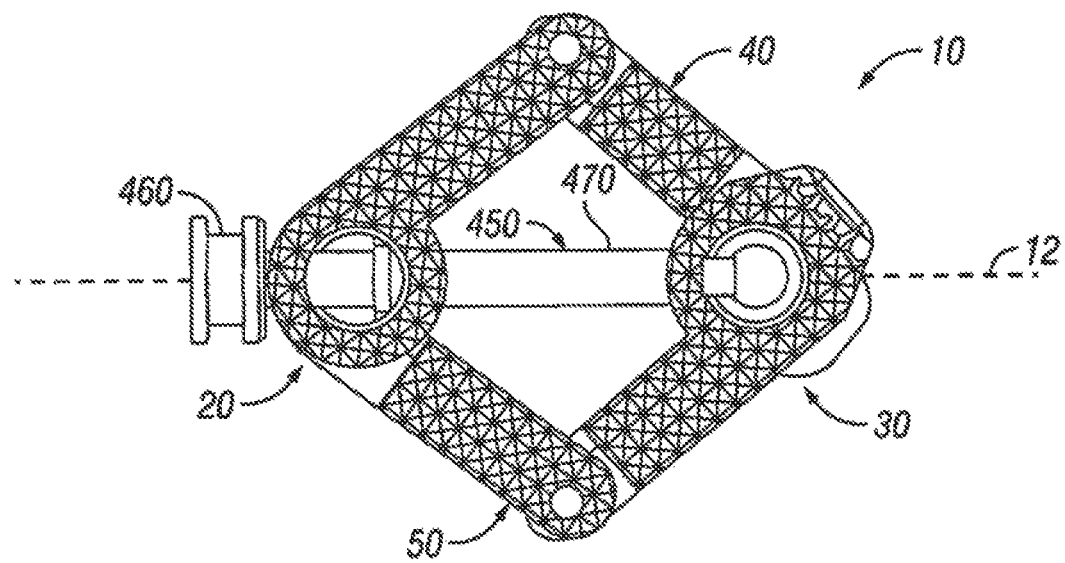
FIG. 22 is a top view of the expandable interbody spacer of FIG. 21 shown in an expanded position.

Referring now to FIGS. 21 and 22, an expandable interbody spacer 10 is illustrated in accordance with another embodiment of the present invention. In the illustrated embodiment, the expandable interbody spacer 10 has a proximal end 20 and a distal end 30. The expandable interbody spacer 10 may include a first jointed arm 40 and a second jointed arm 50 positioned on either side of longitudinal axis 12 of the spacer 10. As illustrated, the expandable interbody spacer 10 further may comprise an internal screw 450. The internal screw 450 may comprise a head 460 and an elongated body 470, which may extend generally parallel to the longitudinal axis 12 of the spacer 10. In some embodiments, the internal screw 450 may extend from the proximal end 20 to the distal end 30 of the spacer 10. In one embodiment, the elongated body 470 may be retractable. For example, the elongated body 470 may retract into the head 460, as shown on FIG. 22.

Figure 23:
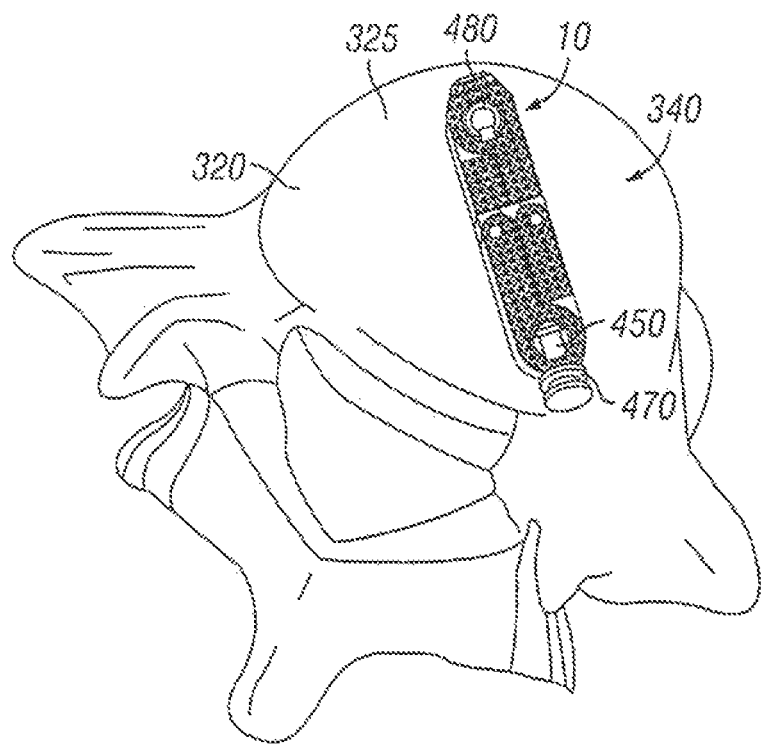
FIG. 23 is a view of the expandable interbody spacer of FIG. 21 shown in a disc space in a collapsed position.
Figure 24:
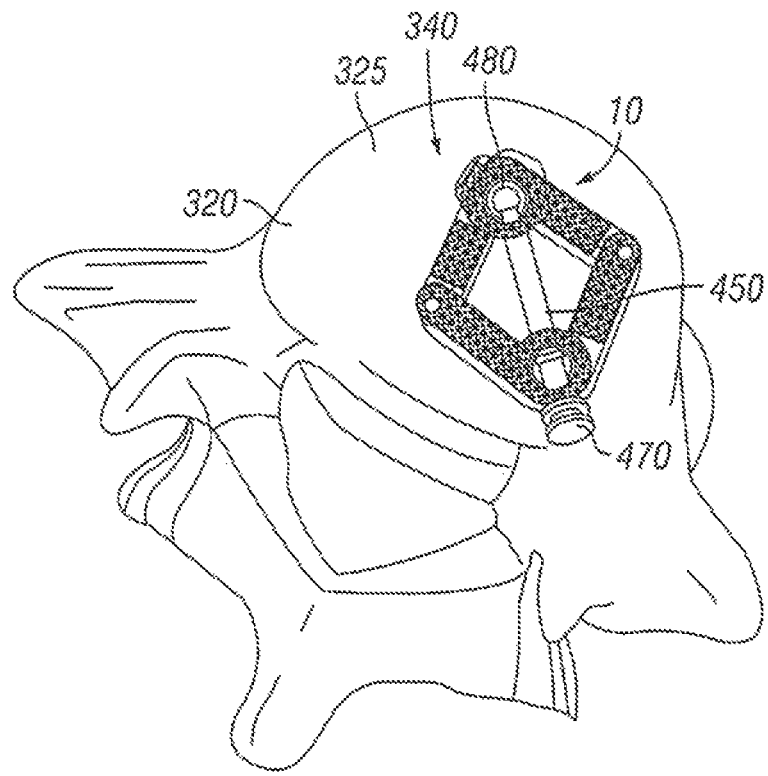
FIG. 24 is a view of the expandable interbody spacer of FIG. 21 shown in a disc space in an expanded position.

As illustrated by FIGS. 23 and 24, the spacer 10 may be introduced into the disc space 330, wherein the spacer 10 can be laterally expanded. In accordance with present embodiments, the spacer 10 can be laterally expanded by folding the first arm 40 and the second arm 50 inward. In some embodiments, the elongated body 470 may be retracted into the head 460 to cause folding of the first arm 40 and the second arm 50 inward, as the first arm 40 and the second arm 50 are secured to the distal end 480 of the internal screw 450.

Figure 25:
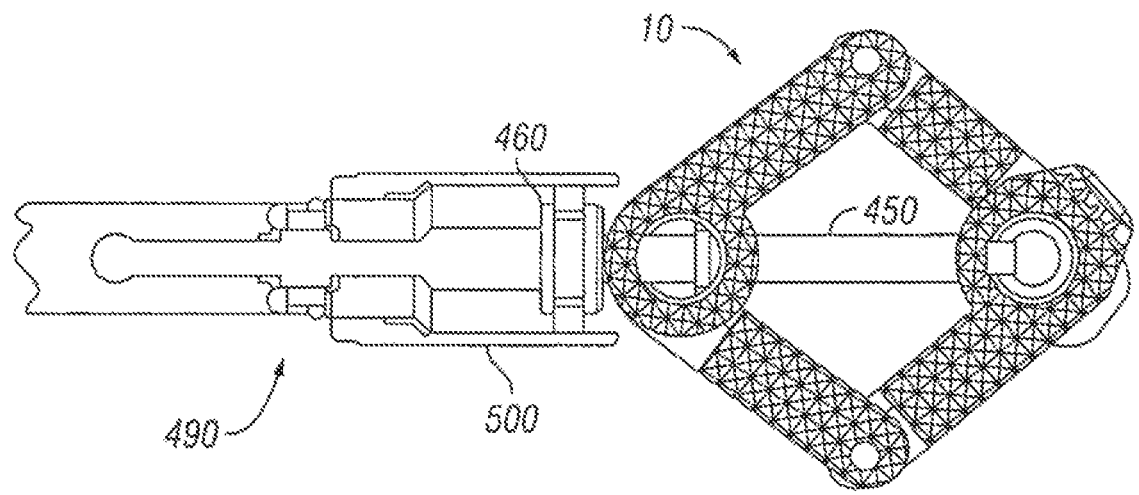
FIG. 25 is a top view of a tool shown engaging the expandable interbody spacer of FIG. 21 in accordance with embodiments of the present invention.
Figure 26:
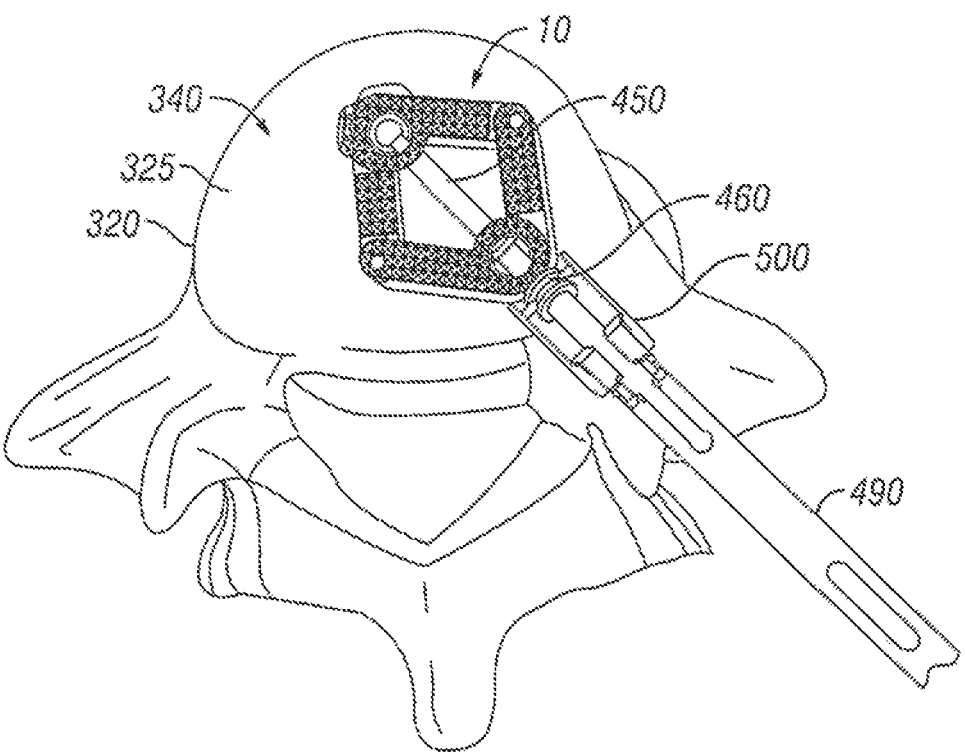
FIG. 26 is a view showing the tool of FIG. 24 expanding the expandable interbody spacer of FIG. 24 in a disc space in accordance with embodiments of the present invention.

FIG. 25 shows attachment of a tool 490 to the expandable interbody spacer 10 of FIGS. 22 and 23 in accordance with embodiments of the present invention. As illustrated, the tool 490 may have an attachment end 500, which can be secured to the head 460 of the internal screw 450. As shown by FIG. 26, the tool 40 can be used to introduce the spacer 10 into the disc space 330, wherein the spacer 10 can be laterally expanded.

Figure 27A:
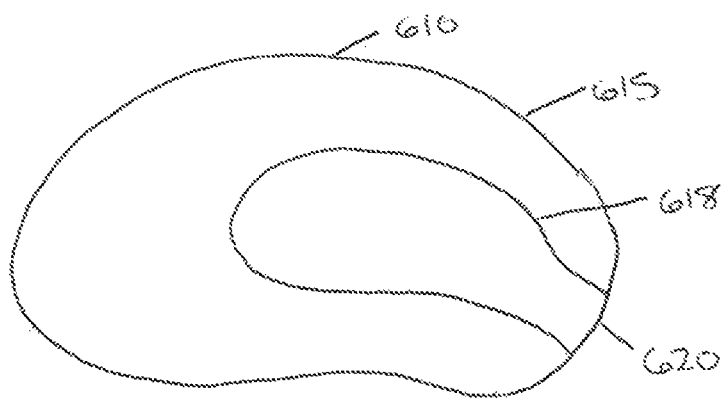
FIGS. 27A-27C show different views of an expandable interbody spacer having an expandable containment bladder in accordance with embodiments of the present invention.
Figure 27B:
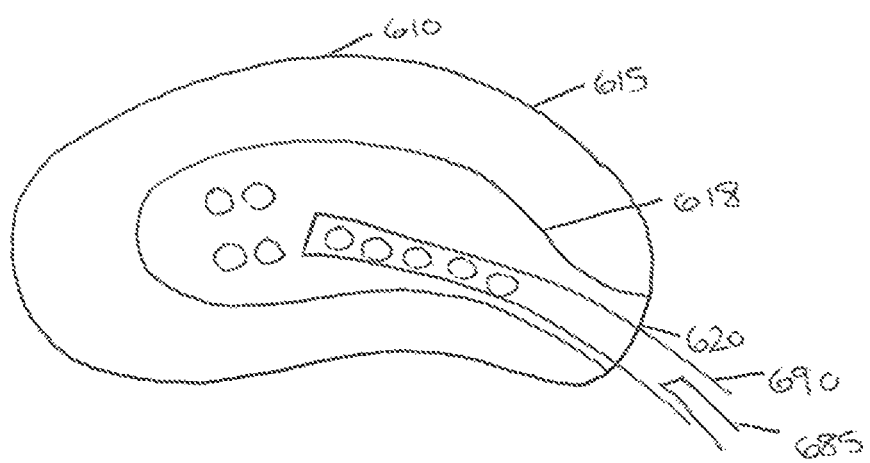

Additional embodiments of expandable interbody spacers are described herein. FIGS. 27A and 27B show top views of an expandable interbody spacer having an expandable containment bladder in accordance with embodiments of the present invention. FIG. 27A illustrates the spacer 610 in an unexpanded state, while FIG. 27B illustrates the spacer 610 in an expanded state.

As shown in FIG. 27A, the spacer 610 comprises an outer body 615 and an inner bladder 618. The inner bladder 618 can include an opening 620 through which an instrument can be inserted to deliver rods or beads that will result in expansion of the spacer 610. In some embodiments, the spacer 610 comprises a convex longitudinal surface opposite a concave longitudinal surface. The spacer 610 can be expanded such that it maintains the convex longitudinal surface and concave longitudinal surface, as shown in FIG. 27B. In other embodiments, expansion of the spacer 610 via rods or beads can result in a configuration that is different from the original shape. Advantageously, the spacer 610 is configured such that a surgeon can deliver rods or beads to thereby transform the spacer 610 into a desired shape to assist in implantation from a variety of different approaches. For example, the spacer 610 can be expanded such that it includes a "banana" type shape that is suitable for transforaminal delivery, or it can be a long, slender shape that is suitable for posterior delivery. In its unexpanded state, the spacer 610 can be easily delivered minimally invasively into a desired anatomical location.

As shown in FIG. 27B, the spacer 610 can receive an instrument 690 through the opening 620 in the inner bladder 618. The instrument 690 can deliver one or more rods or beads 688 that will cause expansion of the inner bladder 618, as well as the overall spacer 610. In some embodiments, the instrument 690 can be a curvable instrument that can deliver the beads 688 to desirable locations within the inner bladder 618, thereby causing selective expansion of the spacer 610. As shown in FIG. 27B, in some embodiments, the spacer 610 can substantially maintain the same shape as in the unexpanded state; however, with the addition of the rods or beads 688, the spacer 610 will be larger and have a much larger footprint than in the unexpanded state. In some embodiments, the overall footprint of the spacer 610 expands along its longitudinal length and/or width, while maintaining a substantially or the same height as the unexpanded spacer 610. In other embodiments, the overall footprint of the spacer 610 expands along its longitudinal length and/or width, and the height of the spacer 610 also changes during expansion.

Figure 27C:
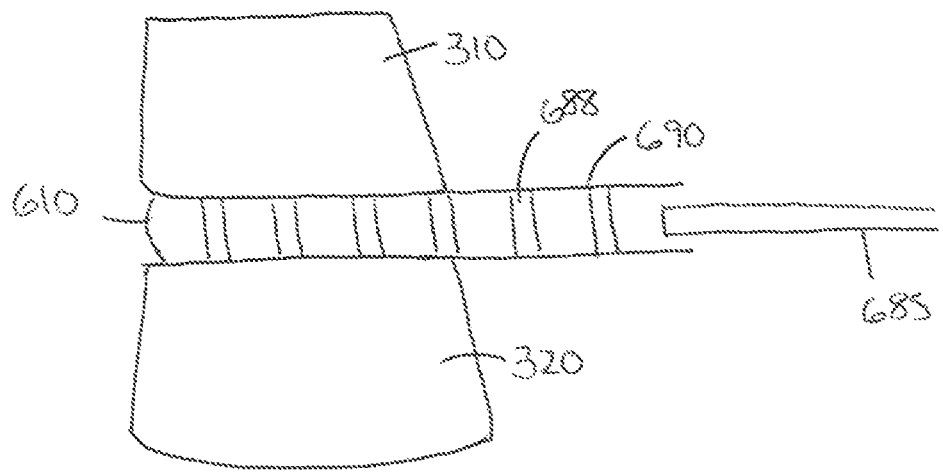

FIG. 27C illustrates a third view of the spacer 610 with the expandable inner bladder 618 inserted between two adjacent vertebrae 310, 320. The spacer 610 is configured to receive one or more rods or beads 688 via the delivery instrument 690. As shown from this view, the delivery instrument 690 can comprise a tubular body that holds the rods or beads 688 in serial formation. The delivery instrument 690 can be accompanied by a pusher instrument 685 that can deliver the rods or beads 688 out in series. In some embodiments, the delivery instrument 690 can also include an automatic depositor such that multiple rods or beads 688 can be delivered in rapid fashion.

Figure 28A:
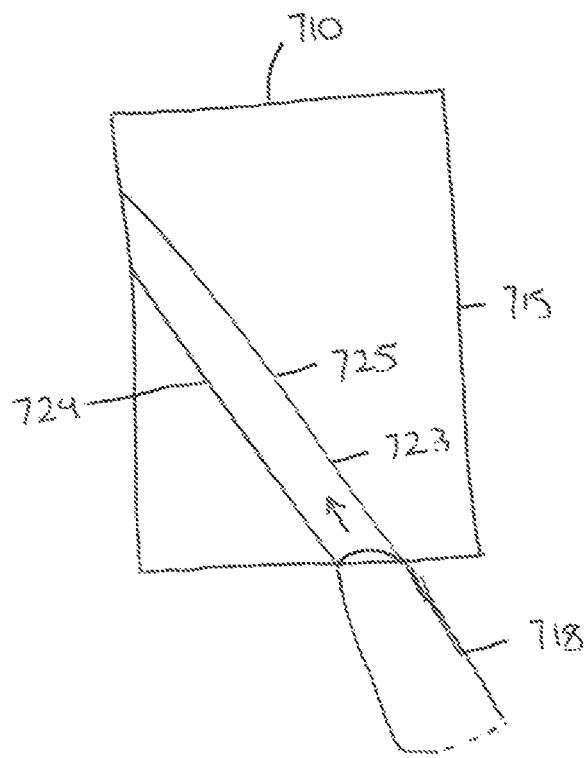
FIGS. 28A and 28B show top views of an expandable spacer utilizing a shim member in accordance with embodiments of the present invention.
Figure 28B:
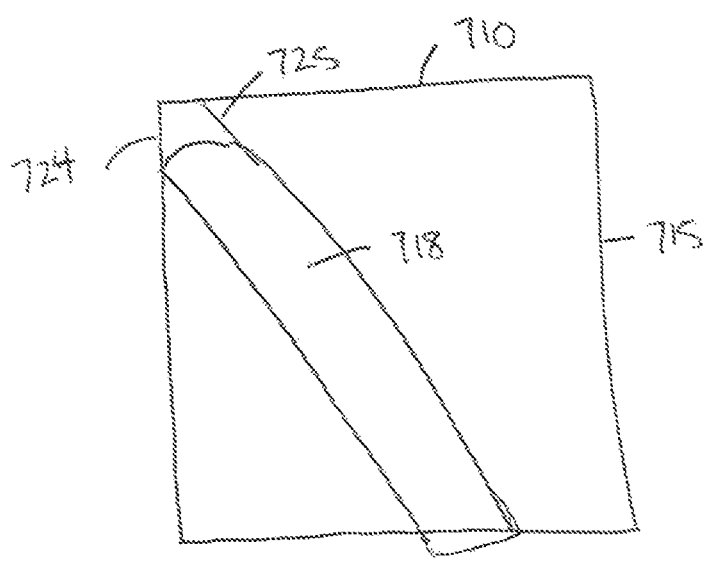

FIGS. 28A and 28B show top views of an expandable spacer utilizing a shim member in accordance with embodiments of the present invention. The expandable spacer 710 comprises an outer body 715 having an opening 718, as shown in FIG. 28A. In some embodiments, the opening 718 is in communication with a channel 723 having opposing walls 724, 725 that extends along a longitudinal axis of the expandable spacer 710. In some embodiments, the channel 723 extends along at least a majority of the length of the expandable spacer. When it is desired to expand the spacer 710, a shim member 720 can be inserted through the opening 718 and into the channel 723, as shown in FIG. 28B. The addition of the shim member 720 causes the spacer 710 to expand by a distance as measured by the increase in distance between the opposing walls 724, 725 of the channel, thereby advantageously increasing the footprint of the spacer 710 once implanted in a desired location. In some embodiments, the shim member 720 is tapered such that the tapering facilitates ease of insertion in the channel 723.

Figure 29B:
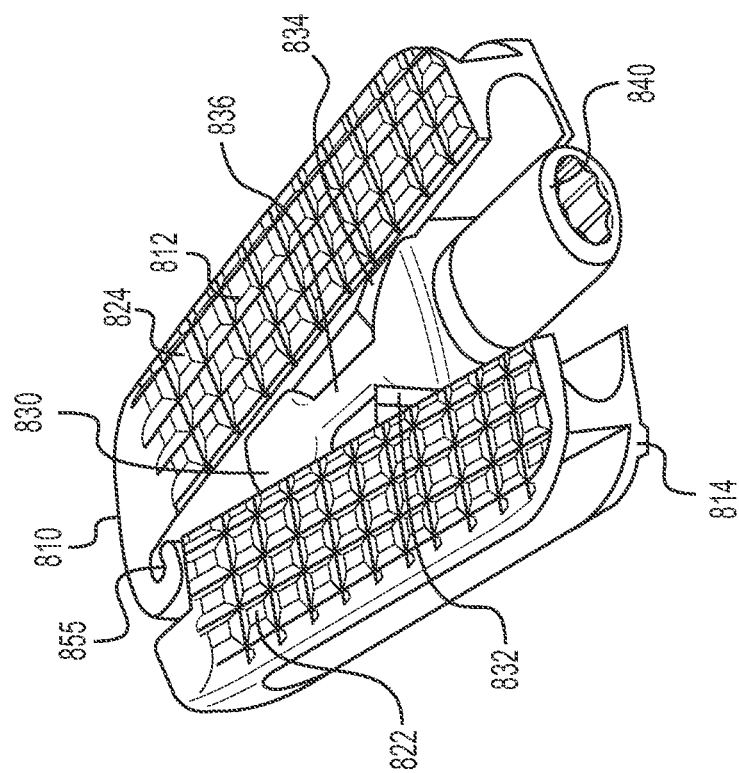
FIGS. 29A and 29B show top perspective views of an expandable spacer utilizing a translation member in accordance with embodiments of the present invention.
Figure 29A:
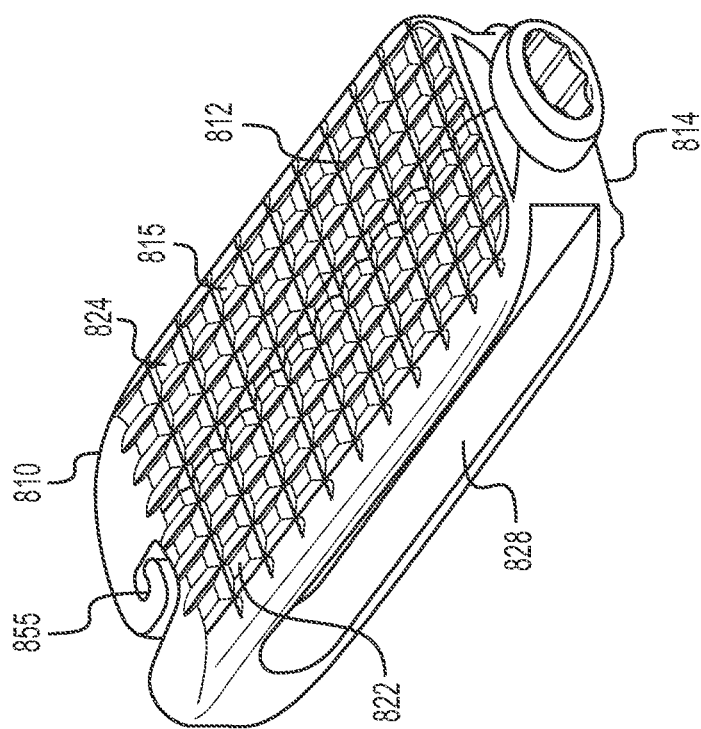

FIGS. 29A and 29B show top perspective views of an expandable spacer utilizing a translation member in accordance with embodiments of the present invention. FIG. 29A illustrates the spacer 810 in a closed configuration, while FIG. 29B illustrates the spacer 810 in an open or expanded configuration.

The expandable spacer 810 comprises an upper endplate 812 and a lower endplate 814. Each of the upper endplate 812 and the lower endplate 814 can include surface texturing 815 thereon to assist in engagement with an adjacent vertebra. In some embodiments, the surface texturing 815 comprises protrusions, teeth, ridges or ribbing. Each of the endplates 812, 814 is formed of two separate members that can be separated from one another laterally in a "v" configuration, as shown in FIG. 29B. With reference to the upper endplate 812, the upper endplate 812 includes a first endplate portion 822 and a second endplate portion 824 that can be separated from one another along a midline 805 that extends through the spacer 810. In some embodiments, at least one of the first endplate portion 822 and the second endplate portion 824 can be connected via a hinge member 855 such that at least one of the endplate portions pivots away from one another. As shown in FIG. 29B, the first endplate portion 822 and the second endplate portion 824 of the upper endplate 812 transition into corresponding members found along the lower endplate 814. In some embodiments, the expandable spacer 810 comprises one or more side slots 828 that can be engaged by an installation instrument to assist in delivery of the spacer 810 to a desired anatomical location.

In order to expand the spacer 810, the spacer 810 includes a translation member 830 and an actuation member 840, as shown in FIG. 29B. The translation member 830 can comprise one or more ramps that engage side ramps formed along inner sidewalls of the spacer 810. As shown in FIG. 29B, the spacer 810 can include at least a pair of ramps 832, 834 that engage with corresponding ramps formed along the inner sidewalls of the spacer 810. As the translation member 830 is translated (e.g., in a first direction), the ramps 832, 834 slide along corresponding ramps formed along the inner sidewalls of the spacer 810, thereby causing expansion of the implant. Translation of the translation member 830 in an opposite direction (e.g., in a second direction) causes contraction of the implant. In some embodiments, the spacer 810 includes more than just the ramps 832, 834. For example, the ramps 832, 834 can be connected via a bridge member 836 to additional ramps along a longitudinal axis of the spacer 810. In some embodiments, ramps 832, 834 are connected via a bridge member 836 to a second pair of ramps that can help with expansion of the spacer 810.

In order to move the translation member 830, in some embodiments, the translation member 830 is operably attached to an actuation member 840. The actuation member 840 can comprise an actuation or set screw 840. In some embodiments, the actuation member 840 includes an opening, such as a hex screw opening, for allowing rotation of the actuation member 840. Rotation of the actuation member 840 in a first direction causes lateral translation of the translation member 830 in the first direction, thereby causing sliding engagement between the ramps 832, 834 of the translation member 830 and ramps of the inner sidewalls, and thus outward expansion of the first endplate portion and second endplate portion. Advantageously, as shown in FIG. 29B, the first endplate portion 822 separates from the second endplate portion 824 in a v-shape, thereby enlarging the footprint of the implant. This advantageously creates an implant with greater load stability, as well as an increased region through which to deposit bone graft material.

Figure 30A:
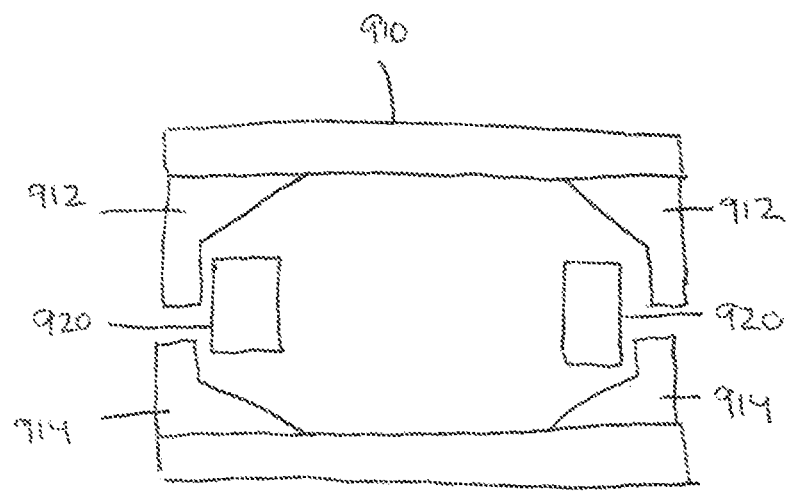
FIGS. 30A and 30B show top views of an expandable spacer including a sliding actuation member in accordance with embodiments of the present invention.
Figure 30B:
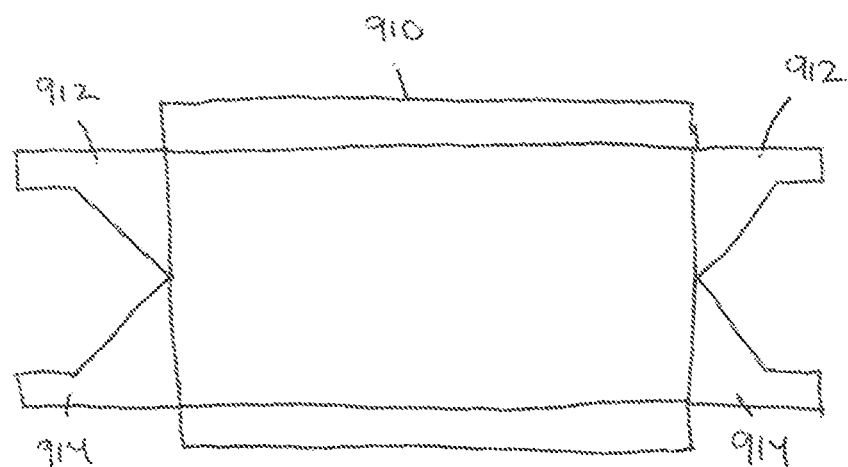

FIGS. 30A and 30B show top views of an expandable spacer including a sliding actuation member in accordance with some embodiments. The expandable spacer 910 includes a pair of upper wing members 912 and a pair of lower wing members 914. As shown in FIG. 30A, an upper wing member 912 and a lower wing member 914 is operably attached to sliding actuation member 920. FIG. 30A illustrates the expandable spacer in an unexpanded configuration. When the spacer is ready for expansion, the sliding actuation member 920 can slide in between the upper wing member 912 and the lower wing member 914, thereby causing the wing members to open outwardly, as shown in FIG. 30B. In some embodiments, the wing members can expand from approximately 12 mm to 20 or more millimeters just by expansion of the wing members.

Figure 31A:
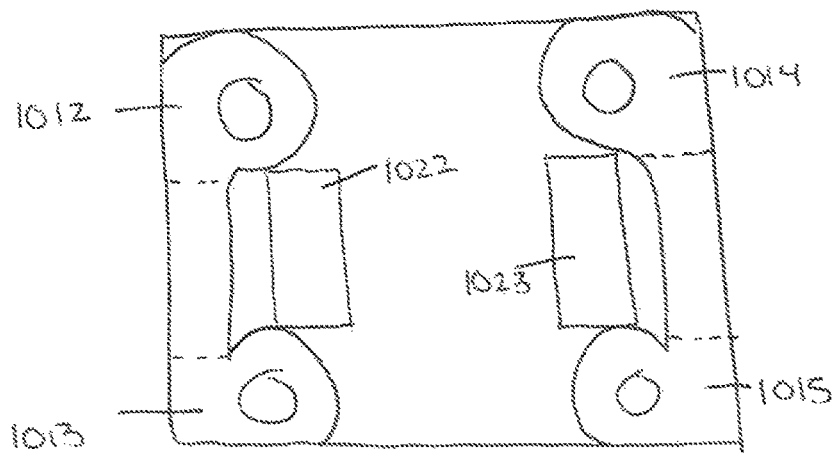
FIGS. 31A and 31B show different views of an expandable spacer having slidable wings in accordance with embodiments of the present invention.
Figure 31B:
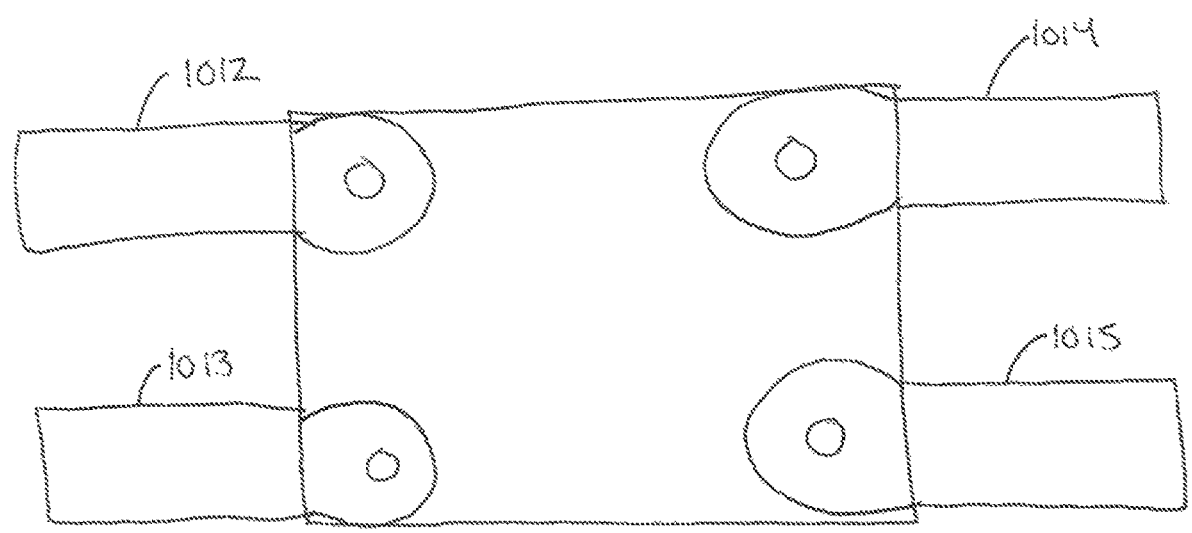

FIGS. 31A and 31B show an alternative embodiment of an expandable spacer having slidable wings in accordance with embodiments of the present invention. The spacer 1010 can be composed of slidable wings 1012, 1013, 1014, 1015. As shown in FIG. 31A, slidable wings 1012, 1013 are on a left side of the spacer 1010, while slidable wings 1014, 1015 are on a right side of the spacer 1010. The spacer 1010 can be delivered to a disc space in a non-expanded, minimally invasive state, as shown in FIG. 31A. Once in the disc space, the wings 1012, 1013, 1014, 1015 of the expandable spacer can be outwardly deployed, thereby causing expansion of the device. In some embodiments, the wings can be complimentary and symmetrical to one another prior to deployment. To deploy the wings, a pre-attached block member 1022, 1023 can be actuated to open the wings. As shown in FIG. 31A, block member 1022 can operate wings 1012, 1013, while block member 1023 can operate wings 1014, 1015. FIG. 31B shows the wings separated and in an expanded state following actuation by the block members.

FIGS. 32A-32D show an expandable spacer comprising an "I-beam" with multiple side slots for receiving complementary side members in accordance with embodiments of the present invention. The spacer 1110 can comprise a central I-beam 1111 with one or more side slots 1116 that receive protruding portions from adjacent side members 1112, 1114. As shown in FIG. 32A, the I-beam and its side members 1112, 1114 complement each other. The I-beam can include a slot 1118 for receiving an actuation member to outwardly expand the side members 1112, 1114. In some embodiments, in a contracted configuration, the side slots 1116 of the I-beam receive the protruding portions 1119 of the adjacent side members 1112, 1114. Upon expansion, the protruding portions 1119 of the adjacent side members will be offset with the side slots 1116 of the I-beam. To offset the protruding portions 1119 of the adjacent side members from the side slots 1116, the I-beam can be slid in a first direction such that the protruding portions move away from the slots. In some embodiments, the protruding portions 1119 can be tapered to allow sliding between the I-beam and the protruding portions. In other embodiments, the actuation member can be any of the actuation components discussed herein for expanding and/or contracting the spacers.

Figure 33B:
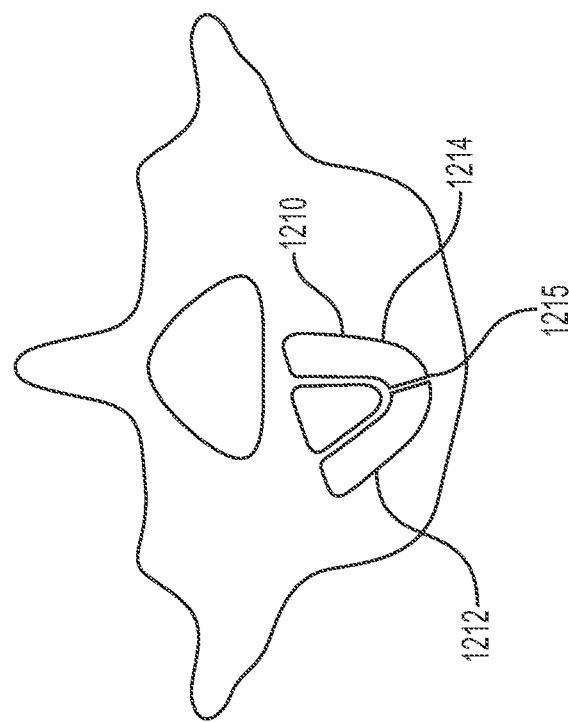
FIGS. 33A and 33B show different views of a hinged expandable interbody spacer in accordance with embodiments of the present invention.
Figure 33A:
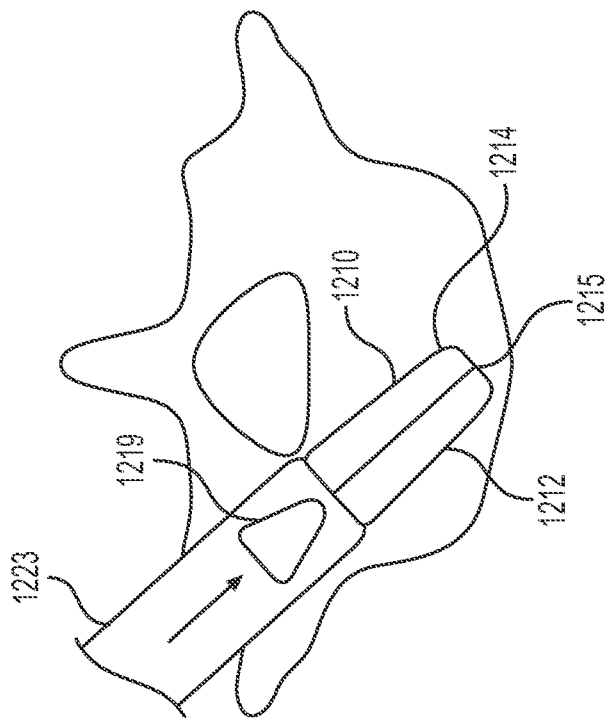

FIGS. 33A and 33B show different views of a hinged expandable interbody spacer in accordance with embodiments of the present invention. FIG. 33A illustrates the spacer 1210 in an unexpanded state and FIG. 33B illustrates the spacer 1210 in an expanded state within a vertebral space 3. As shown in FIG. 33A, the spacer 1210 can comprises two expandable portions 1212, 1214 that are connected to each either by a hinge joint 1210. In the unexpanded state, the two expandable portions 1212, 1214 of the spacer 1210 can be positioned side-by-side or adjacent to one another. In some embodiments, inner facing side surfaces of the two expandable portions 1212, 1214 are in direct contact with one another in the unexpanded state.

To expand the spacer 1210, a wedge member 1219 can be delivered in between the two expandable portions 1212, 1214. The wedge member 1219 can be inserted where the inner side surfaces of the expandable portions 1212, 1214 meet, thereby separating the first expandable portion 1212 from the second expandable portion 1214. As the first expandable portion 1212 and the second expandable portion 1214 are connected via a hinge 1215, the spacer 1210 will assume an expanded v-shape upon expansion, as shown in FIG. 33B. In some embodiments, the wedge member 1219 can comprise a triangular wedge member. As shown in FIG. 33B, the wedge member 1219 can be placed substantially adjacent to or in contact with the hinge 1215 in some embodiments. In some embodiments, in the expanded configuration, the wedge member 1219 can advantageously remain embedded within the v-shape of the expanded spacer 1210, thereby preventing closing or contraction of the expanded configuration.

In some embodiments, the wedge member 1219 can be accompanied by an insertion instrument 1223 to assist in delivery of the wedge member 1219. The wedge member 1219 can comprise a proximal end and a distal end that is directly adjacent and/or in contact with the expandable portions 1212, 1214. The insertion instrument 1223 includes a sleeve to guide the wedge member 1219 to a desired location between the hinged expandable portions 1212, 1214.

Figure 34A:
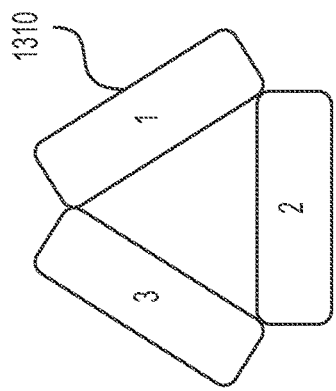
FIGS. 34A-34D show different views of an alternate hinged expandable interbody spacer in accordance with embodiments of the present invention.
Figure 34B:
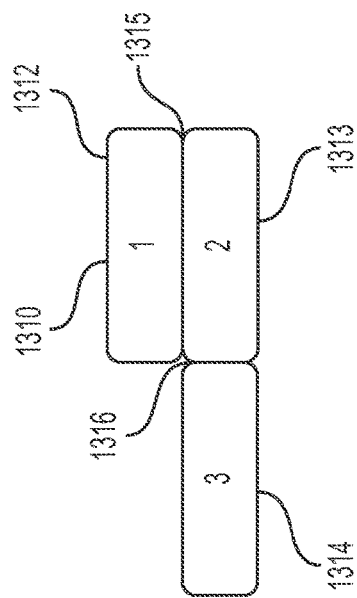

FIGS. 34A-34D show different embodiments of an alternative hinged spacer 1310 in accordance with some embodiments. FIG. 34A illustrates a hinged spacer 1310 in an unexpanded configuration, while FIG. 34B illustrates the hinged spacer 1310 in an expanded configuration. The hinged spacer 1310 comprises a first expandable portion 1312, a second expandable portion 1313, and a third expandable portion 1314 that are connected to one another via hinges 1315, 1316.

Figure 34C:
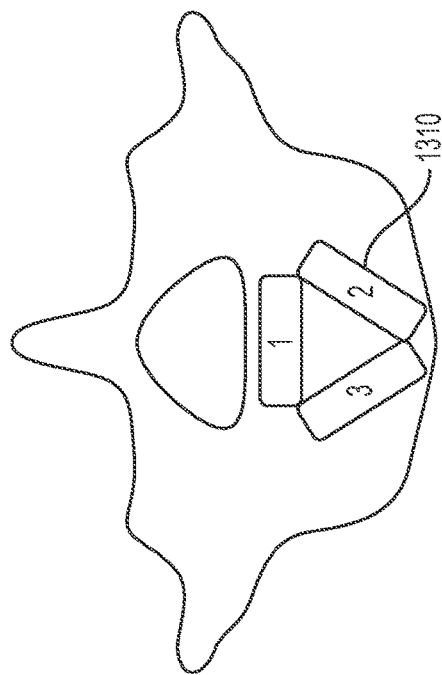
Figure 34D:
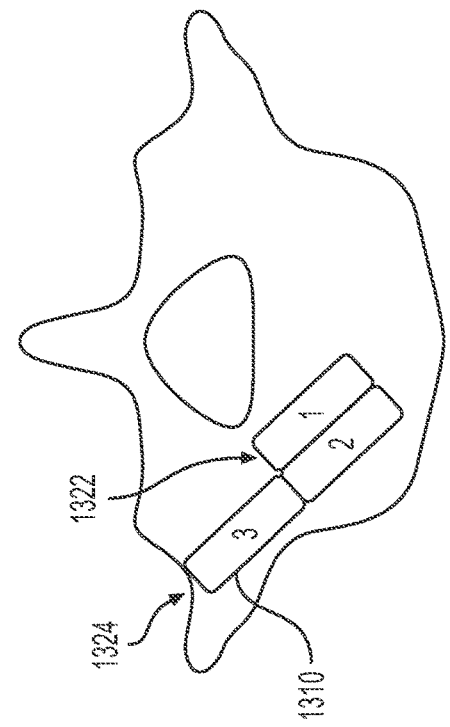

In order to expand the hinged spacer 1310, the spacer 1310 advantageously provides a holding point 1322 and a pushing point 1324 (as shown in FIG. 34C). The holding point 1322 is a point at which an insertion instrument can steadily hold the spacer 1310. In some embodiments, an insertion instrument will hold the spacer 1310 by gripping a surface. In other embodiments, an insertion instrument can engage the spacer 1310 via one or more insertion surfaces (e.g., a threaded hole) that are formed in the holding point 1322. While the spacer 1310 is being held at its holding point 1322, the insertion instrument can further comprise a pusher that expands the spacer 1310 by applying a force on the surface of the pushing point 1324. In some embodiments, a pushing instrument that is separate from the insertion instrument can be used (e.g., inserted through the insertion instrument) such that it causes expansion of the spacer 1310. As shown in FIGS. 34C and 34D, the expandable spacer 1310 can advantageously be expanded in situ.

Figure 35B:
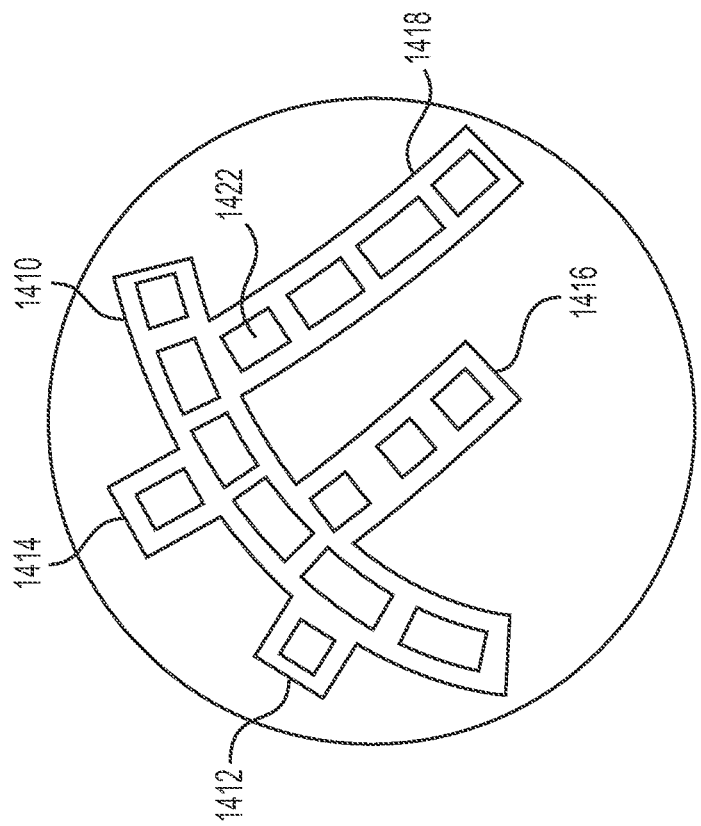
FIGS. 35A and 35B show an expandable spacer including a flexible containment member in accordance with some embodiments.
Figure 35A:
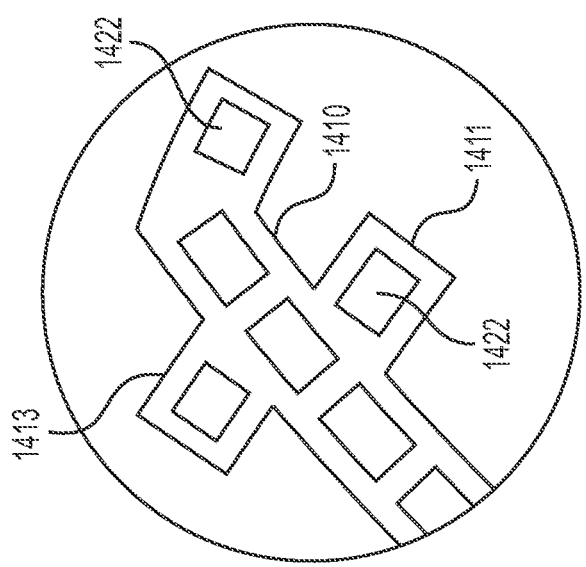

FIGS. 35A and 35B show an expandable spacer including a flexible containment member in accordance with some embodiments. FIG. 35A illustrates the spacer 1410 in an unexpanded state, while FIG. 35B illustrates the spacer 1410 in an expanded state within a disc space 3. The expandable spacer 1410 can comprise a flexible containment structure 1411 that includes one or more channels 1413 for receiving blocks 1422. Insertion of the blocks 1422 causes the channels to fill, thereby causing expansion of the spacer 1410. Advantageously, the flexible containment structure 1411 can be inserted into a disc space with few if any blocks such that the spacer 1410 can be inserted through as small an incision as possible. After the spacer 1410 is placed in a desired position in a disc space, blocks 1422 can be added into the flexible containment structure 1411 to fill the channels, thereby causing expansion of the spacer 1410 in situ.

The flexible containment structure 1411 of the spacer 1410 can comprises one or more channels to accommodate the blocks. As shown in FIG. 35B, the flexible containment structure 1411 can include a number of channels 1412, 1414, 1416, 1418. In some embodiments, the channels are of a same size and shape, while in other embodiments, the channels can be of a different size and shape in order to more closely approximate the desired anatomical shape of the disc space. In some embodiments, the flexible containment structure 1411 can be comprised of a flexible material, such as a plastic, a rubber, or other elastomeric material. In some embodiments, the flexible containment structure 1411 can comprise a woven or braided member that expands with the addition of the blocks.

To assume their expanded configuration, the channels 1412, 1414, 1416, 1418 of the flexible containment structure 1411 are configured to receive one or blocks 1422 in each of the channels in order to for them to reach their maximum size. In some embodiments, the channels can each receive the same number of blocks, while in other embodiments (as shown in FIG. 35B), the channels can receive different numbers of blocks. Advantageously, by providing channels that accommodate a different number of blocks, a specific anatomical footprint can be achieved within the disc space that caters to different patients of different sizes. In some embodiments, the blocks 1422 can be formed of a polymeric material, such as PEEK.

In some embodiments, an instrument is capable of directing the blocks 1422 to individual channels in order to cause selective expansion of the implant 1410. In other embodiments, the blocks 1422 fill the channels themselves without any specific directing by an instrument. The channels can be made of a distinct size such that upon filling, the blocks 1422 will fill other regions of the implant 1410, without having to be directed by an insertion instrument.

Figure 36:
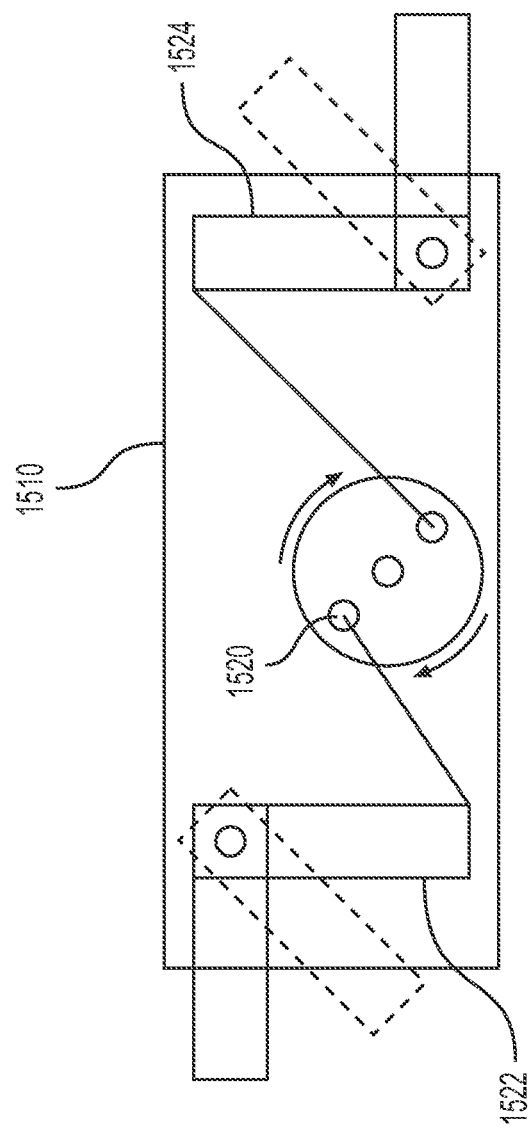
FIG. 36 shows an expandable spacer including a rotating cam to actuate expandable wings in accordance with some embodiments.

FIG. 36 shows an expandable spacer 1510 including a rotating cam to actuate expandable wings in accordance with some embodiments. Rotation of the cam 1520 in a first direction causes wings 1522, 1524 to outwardly expand, wherein rotation of the cam 1520 in a second direction opposite the first causes wings 1522, 1524 to inwardly contract.

Figure 37A:
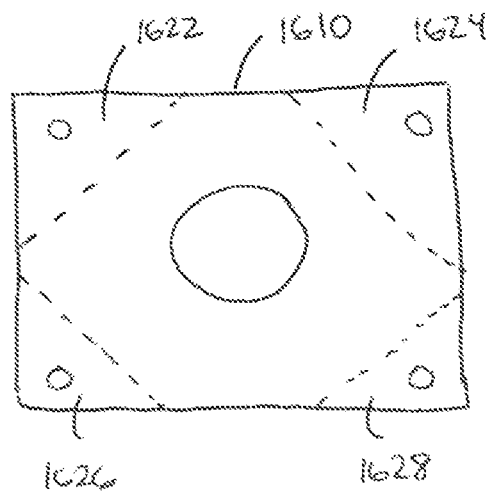
FIGS. 37A and 37B show an expandable spacer including four wings actuated by a gear mechanism in accordance with some embodiments.
Figure 37B:
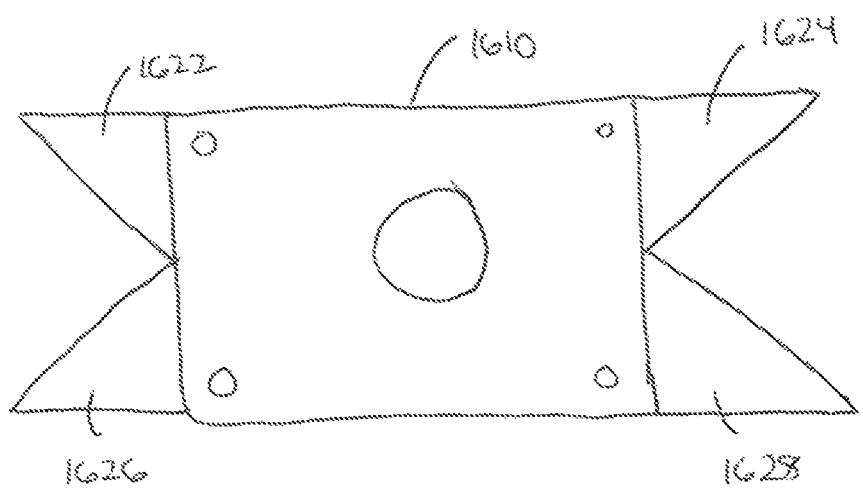

FIGS. 37A and 37B show an expandable spacer including four wings actuated by a gear mechanism in accordance with some embodiments. The spacer 1610 comprises four wings 1622, 1624, 1626, 1628 that can be kept in a contracted state (FIG. 37A) and then expanded into an expanded state (FIG. 37B) using a gear mechanism 1630. Advantageously, the gear mechanism, which can include levers, pivoting arms, etc., can control the expansion of the wings such that the wings need not be fully expanded. In other words, the expandable spacer 1610 can have a series of increased expansion widths, rather than just a single contracted state and a single expanded state.

Figure 38B:
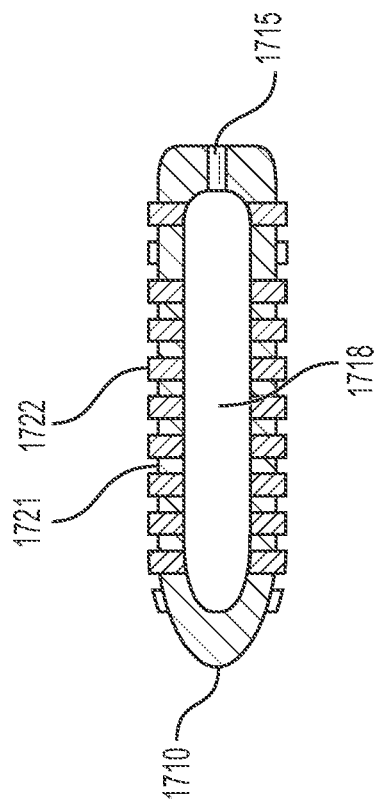
FIGS. 38A and 38B show an expandable spacer including deployable pins in accordance with some embodiments.
Figure 38A:
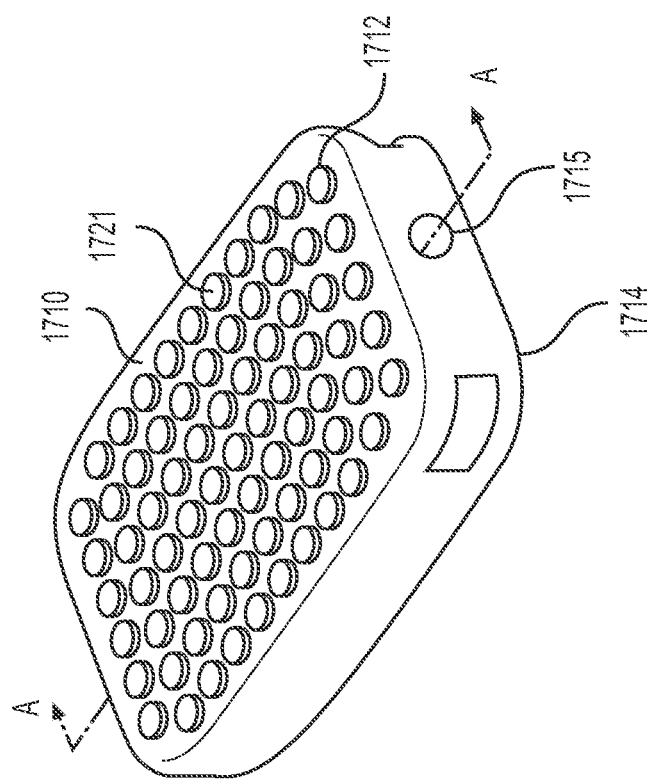

FIGS. 38A and 38B show an expandable spacer 1710 comprising deployable pins in accordance with some embodiments. In contrast to prior spacers that expand to provide a greater footprint in a disc space, the present spacer 1710 (via its pins 1722) expands in a superior and/or inferior direction in order to conform superior and inferior endplates 1712, 1714 of the spacer 1710 with adjacent vertebrae.

FIG. 38A illustrates the spacer 1710 in an unexpanded state. The spacer 1710 comprises a superior endplate 1712 and an inferior endplate 1714 having a plurality of holes or openings 1721 therethrough. Within the openings 1721 are a plurality of deployable pins 1722 that can outwardly expand through the openings 1721 in order to increase the height of the spacer within the disc space. In some embodiments, the spacer 1710 body can comprise a port 1715 for receiving an expandable member 1718 (shown in FIG. 38B) that can outwardly deploy the pins to increase the height of the spacer 1710.

FIG. 38B illustrates the spacer 1710 in an expanded state. From this view, one can see an expandable member 1718 within the body of the spacer 1710. Expansion of the expandable member 1718 within the body of the spacer 1710 causes the deployable pins 1722 to expand outwardly, thereby increasing the height of the spacer 1710. In some embodiments, the expandable member 1718 can comprise a balloon member. In some embodiments, an expansion instrument is insertable through the port 1715. The expansion instrument is capable of inflating or enlarging the expandable member 1718. As the expandable member 1718 expands, exterior surfaces of the expandable member 1718 push against the deployable pins 1722, thereby causing the pins 1722 to protrude outwardly and cause overall height expansion of the spacer 1710.

Figure 39:
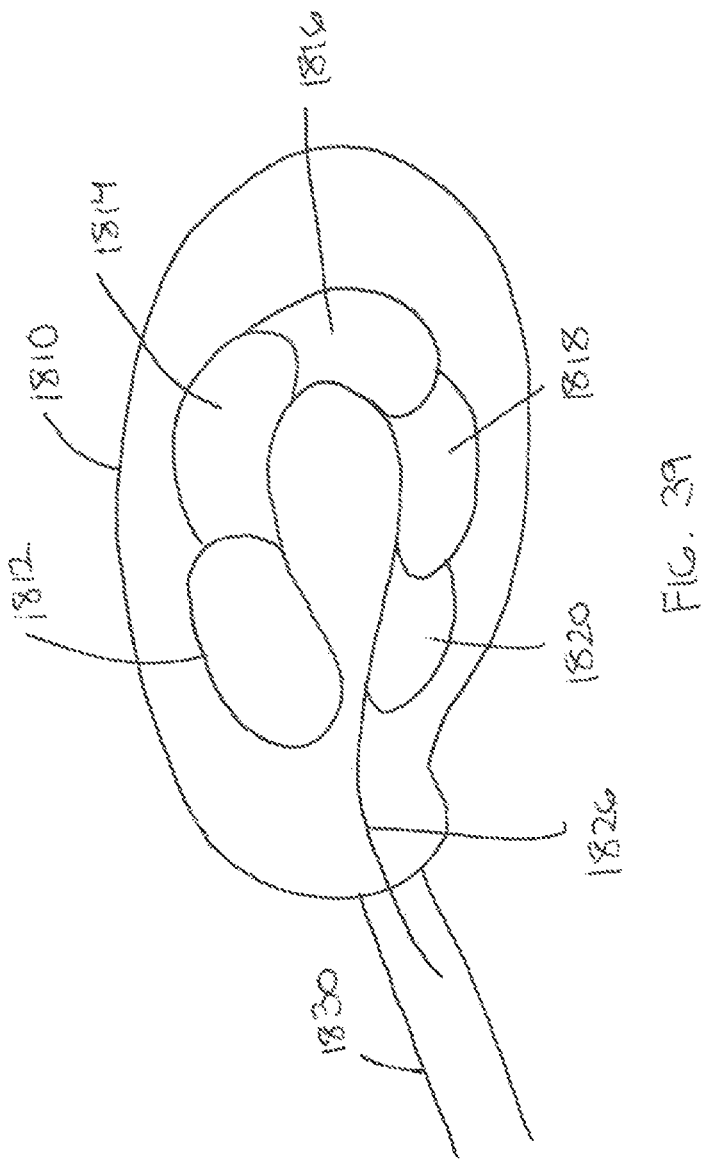
FIG. 39 shows an expandable spacer expandable via a guide wire in accordance with some embodiments.

FIG. 39 shows an expandable spacer expandable via a guide wire in accordance with some embodiments. The spacer 1810 comprises two or more linked members that can be fed into a disc space via a guide wire. Advantageously, the spacer 1810 can be inserted into a small incision that is about the width of a single linked member. The linked members can be attached to a guide wire or k-wire 1826 that extends through each of the linked members. As the spacer 1810 is fed into the disc space, the natural anatomy of the disc space causes the linked members to curve and expand to widen the footprint of the device. As shown in FIG. 39, the spacer 1810 can comprise at five linked members 1812, 1814, 1816, 1818, 1820. In other embodiments, the spacer 1810 comprises less than five linked members or greater than five linked members. The linked members can be connected to adjacent members via a joint 1824 (such as a hinge joint). Each of the linked members can include an opening for receiving the k-wire 1826. Following expansion of the implant in situ, the k-wire 1826 can be removed, thereby leaving the implant in place. The k-wire 1826 can be delivered by an instrument 1830.

Figure 40:
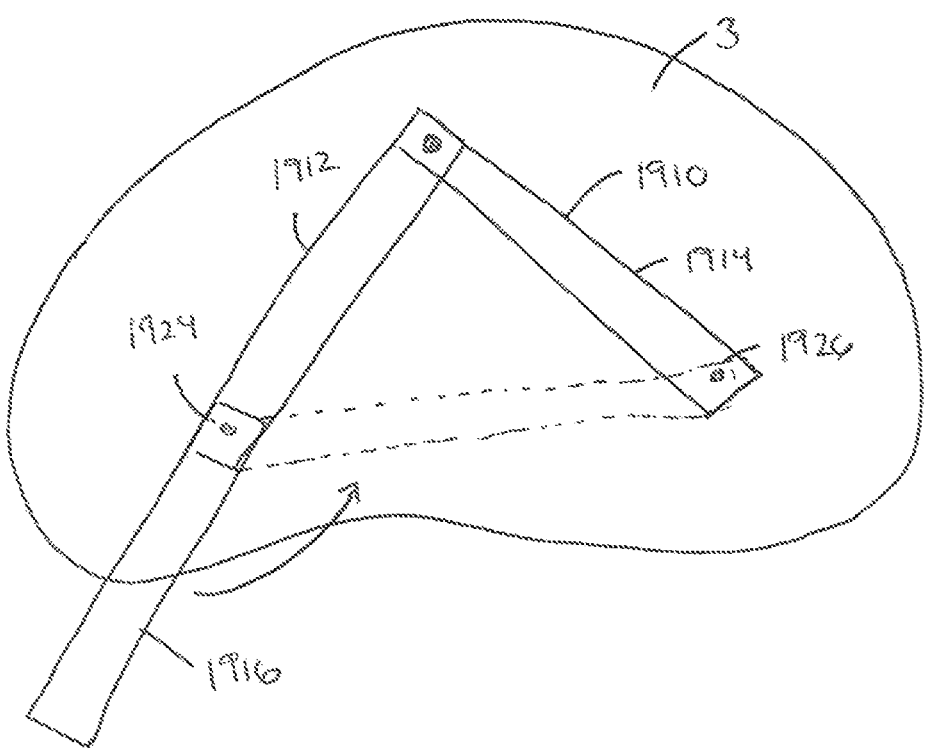
FIG. 40 shows an expandable spacer including an add-on member in accordance with some embodiments.
Figure 42B:
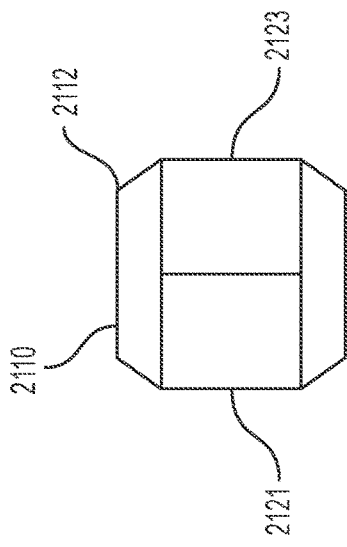
FIGS. 42A-D show a rotatable spacer capable of expansion following rotation in accordance with some embodiments.
Figure 42D:
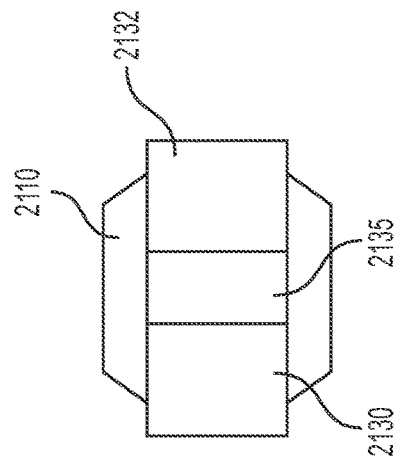
Figure 42A:
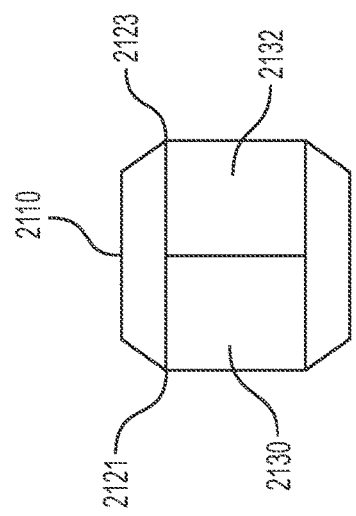
Figure 42C:
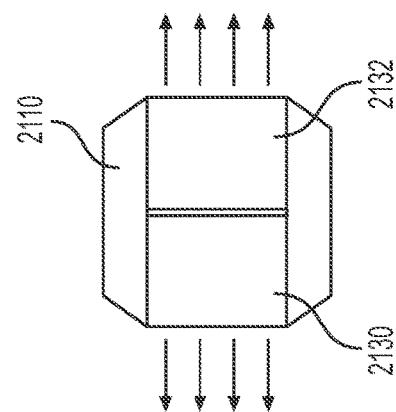

FIG. 40 shows an expandable spacer including an add-on member in accordance with some embodiments. This spacer 1910 includes a first member 1912 and a second member 1914 that can be inserted into a disc space 3 on their own. As shown in FIG. 40, the first member 1912 and the second member 1914 can be elongated members in the form of rods that are joined together at a hinge or joint 1922. The first member 1912 and the second member 1914 can be inserted in a configuration whereby the two members are in contact with each other. Once the first member 1912 and the second member 1914 are inserted into the disc space 3, the two members can be expanded into a V-shape configuration, such that they are ready to receive a third add-on member 1916.

The third add-on member 1916 can be inserted into the disc space 3 and can be attached to the first member 1912 and second member 1914 at respective joints or hinges 1924, 1926. In some embodiments, the third add-on member 1916 can be snap-fitted to the first two members. In other embodiments, the first member 1912 and the second member 1914 include openings near the joints 1924, 1926 for receiving the third add-on member 1916 easily therethrough. With the third add-on member 1916, the implant can assume the shape of a triangle that advantageously has a large footprint within the disc space 3. Bone graft material can be provided into the completed spacer 1910, thereby helping to aid in a fusion process within the disc space.

FIG. 41 shows a buildable spacer 2010 that can be guided by tracks in a disc space to form a large footprint in a disc space in accordance with some embodiments. In this embodiment, multiple tracks 2022, 2024, 2026 can be formed within a disc space 3 to guide individual spacer members 2012, 2014 into desired positions within the disc space. The tracks 2022, 2024, 2026 can be pre-laid within a disc space prior to inserting the spacer members 2012, 2014. In some embodiments, the tracks 2022, 2024, 2026 can compose tracks formed by the disc space itself (e.g., a surgeon can form the tracks out of the cut bone), while in other embodiments, the tracks 2022, 2024, 2026 can be formed by inserted materials within the disc space, such as metals, polymers or bone material. Once the tracks 2022, 2024, 2026 have been laid, individual spacer members 2012, 2014 in the form of elongated members or rods can be inserted and guided by the individual tracks, thereby creating a spacer with an expanded footprint in situ. Advantageously, in some embodiments, the spacer members 2012, 2014 can be inserted individually into the disc space, thereby requiring a small incision. As the spacer members 2012, 2014 are guided in the track, the spacer 2010 size is increased. In some embodiments, there are more tracks than spacer members, thereby advantageously providing multiple options for configuring the implant in situ.

FIGS. 42A-D show a rotatable spacer capable of expansion following rotation in accordance with some embodiments. The spacer 2110 comprises a pair of expandable panels 2130, 2132 that are capable of expansion following rotation of the spacer 2110 in a disc space. The spacer 2110 includes a leading edge 2112, a trailing edge 2114, a bottom surface 2121 and a top surface 2123. The spacer 2110 can be inserted in a first direction in a minimally invasive manner via its leading edge 2112. Once within the disc space, the spacer 2110 can be rotated, such as 90 degrees. After rotation, the panels 2130, 2132 of the spacer 2110 can be advantageously expanded, thereby exposing a graft slot 2135 therein. In some embodiments, the footprint of the spacer 2110 can increase by at least 20-30 percent. For example, in some embodiments, the width of the spacer 2110 can expand from an initial 20 mm width to at least a 30 mm width, with a desirable volume in the middle of the spacer 2110 for receiving graft material.

FIGS. 43A-C show an expandable spacer capable of outward folding in accordance with some embodiments. The spacer 2210 comprises a first section 2212 and a second section 2214 that are operably connected via a joint or hinge 2218. As shown in FIG. 43A, the spacer 2210 can have a minimally invasive configuration whereby the first section 2212 and the second section 2214 are inwardly folded together.

Once the spacer 2210 is inserted into a disc space, the spacer 2210 can be expanded whereby its first section 2212 and second section 2214 are outwardly folded. As shown in FIG. 43B, the spacer 2210 in its expanded state can reveal surface protrusions or teeth 2220 along at least portion of the first and second sections 2212, 2214. In some embodiments, the surface protrusions 2220 extend along a majority of the perimeter of each of the first and second sections 2212, 2214. These surface protrusions 2220 advantageously provide a gripping surface to prevent extrusion of the spacer 2210 once it has been expanded within a disc space.

FIG. 43C illustrates an alternative embodiment of the spacer 2210. In some embodiments, the expanded spacer 2210 can reveal multiple embedded layers. The spacer 2210 can have first and second outer sections 2212a, 2214a, first and second mid sections 2212b, 2214b and first and second inner sections 2212c, 2214c. Each of these sections can include surface protrusions or teeth. With the multiple embedded layers, the spacer 2210 advantageously provides greater surface area for engagement with adjacent vertebrae and also a greater covered footprint for better loading distribution.

Figure 44A:
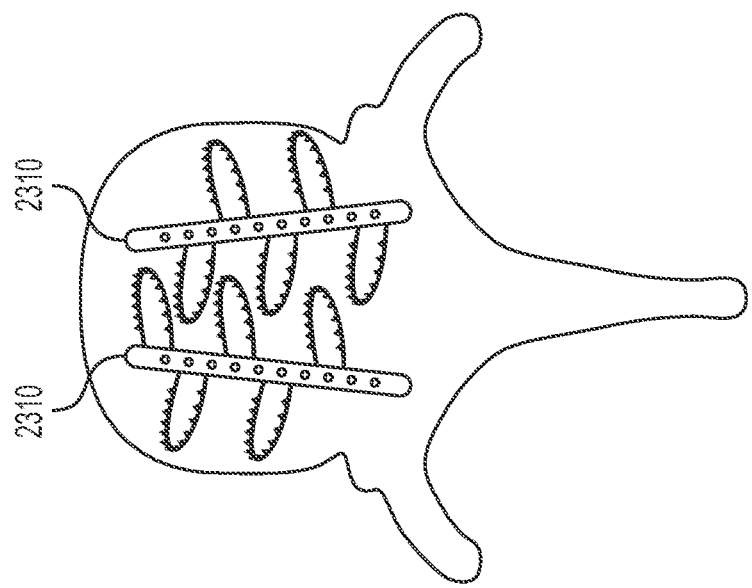
FIGS. 44A and 44B show a pair of expandable spacers having deployable arms.
Figure 44B:
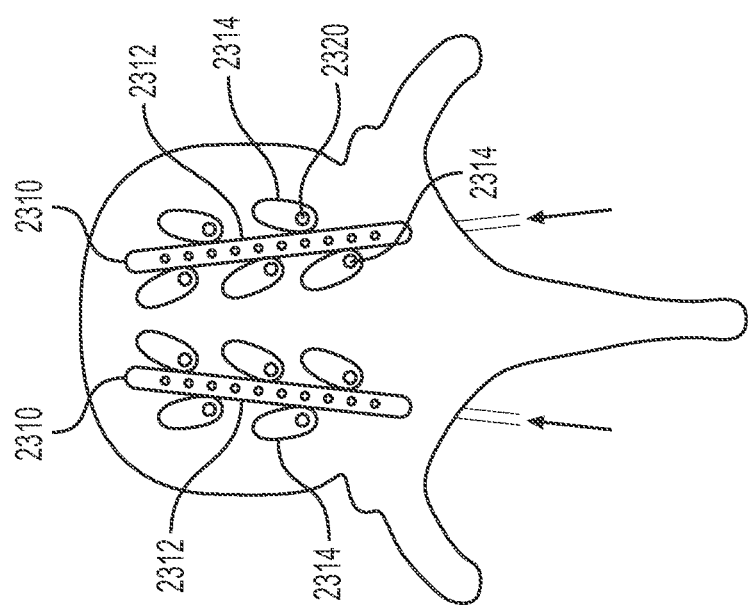

FIGS. 44A and 44B show a pair of expandable spacers having deployable arms. The spacers 2310 comprise an elongated body 2312 having one or more arms 2314 extending from the body 2312. In some embodiments, the arms 2314 are flexible members that can be bent along the length of the body 2312 prior to deployment, thereby providing for minimally invasive insertion. In other embodiments, the arms 2314 are more rigid members that can be deployed via an instrument that can be inserted through the body 2312 of the spacer 2310. For example, when the arms 2314 are ready for deployment, an instrument can be inserted along the length of the body 2312 to release or outwardly rotate the deployable arms 2314. In other embodiments, the arms 2314 can be inflatable, such as by adding an expandable medium into the arms.

FIG. 44A shows the spacer 2310 in an unexpanded configuration, while FIG. 44B shows the spacer 2310 in an expanded configuration with the arms 2314 deployed. With the arms outwardly deployed, the spacer 2310 advantageously has a larger footprint in a disc space compared to when it is first inserted into the disc space. In addition, in some embodiments, one or more arms 2314 can include one or more ports 2320. Advantageously, these ports 2320 can serve as graft windows, such that graft material can be delivered therein. While the illustrated embodiment shows the arms 2314 as having a single port in each arm, in other embodiments, two or more ports can reside on the arms. Moreover, in some embodiments, the elongated body 2312 can also include ports or graft windows for receiving bone graft material therein.

Figure 45A:
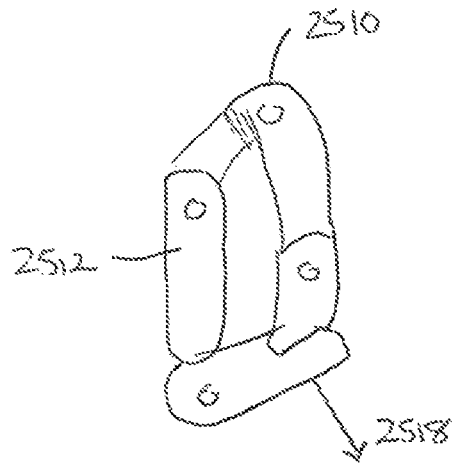
FIGS. 45A-45C show an expandable spacer having a rack and pinion actuator in accordance with some embodiments.
Figure 45B:
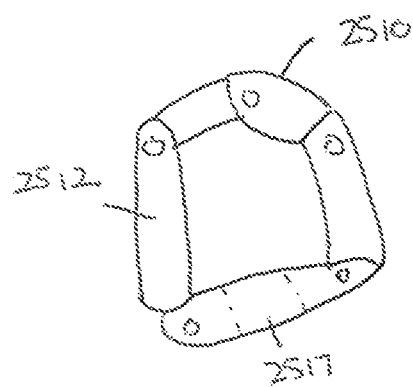
Figure 45C:
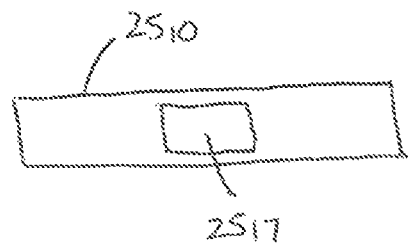

FIGS. 45A-45C show an expandable spacer having a rack and pinion actuator in accordance with some embodiments. The spacer 2510 comprises two or more linking members 2512 that are joined together at joints or hinges. In some embodiments, the spacer 2510 can include a rack and pinion actuator that allows the spacer to be pulled in the direction 2518. The rack and pinion actuator advantageously allows the spacer to expand incrementally, thereby allowing a surgeon to control the shape of the spacer within different types of patients. In some embodiments, the rack and pinion spacer will be controlled to sit on an apophyseal ring of the patient, thereby providing desirable load distribution when in use. In some embodiments, the spacer 2510 can include a graft window 2517 that can receive graft material therein.

Figure 46A:
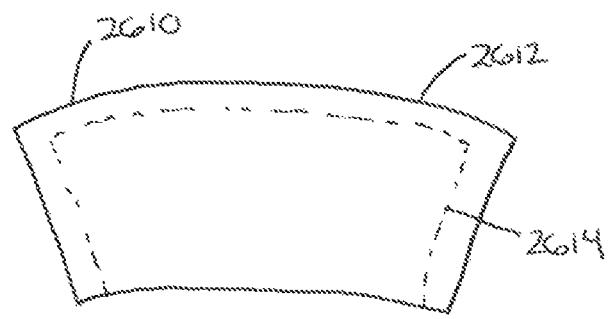
FIGS. 46A-46C show an expandable spacer having an outer member with a slidable inner member therein.
Figure 46B:
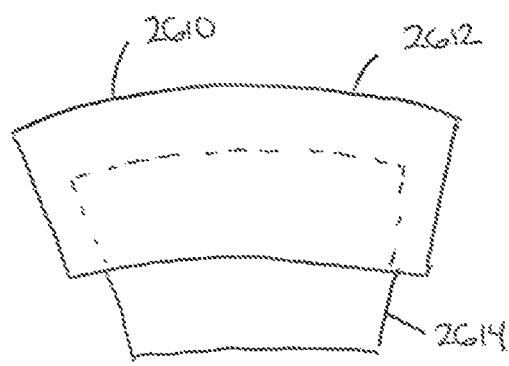
Figure 46C:
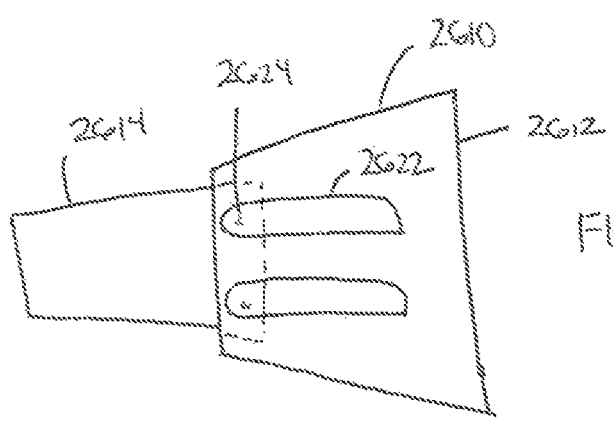
Figure 47A:
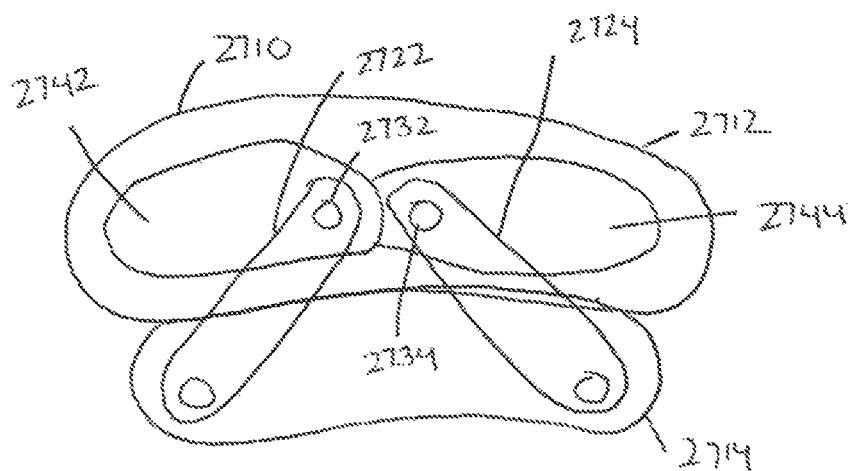
FIGS. 47A and 47B show an expandable spacer having upper and lower members separated by linking members in accordance with some embodiments.

FIGS. 46A-46C show an expandable spacer having an outer member with a slidable inner member therein. The spacer 2610 comprises an outer member 2612 including an inner member 2614 capable of sliding in and out of the outer member 2612. As shown in FIG. 47A, the spacer 2610 can have a first, unexpanded configuration whereby the inner member 2614 is substantially within the body of the outer member 2612. After being inserted into a disc space, the inner member 2614 can be slid outward from the outer member 2612, thereby causing expansion of the spacer 2610 and a greater footprint.

FIG. 46C shows a side view of the expandable spacer and a mechanism for sliding the inner member 2614 out of the outer member 2612 according to some embodiments. In some embodiments, in order to slide the inner member 2614 in and out of the outer member 2612, the inner member 2614 can include pin members 2624 that ride in slots 2622 formed in the outer member 2612, until a desired expansion of the inner member 2614 is reached. In some embodiments, the pin members 2624 can be locked at any point along the length of the slots, such as by rotating the pin members 2624. In other embodiments, the pin members 2624 have designated unlocking/locking points, located at designated parts of the slots 2622.

Figure 47B:
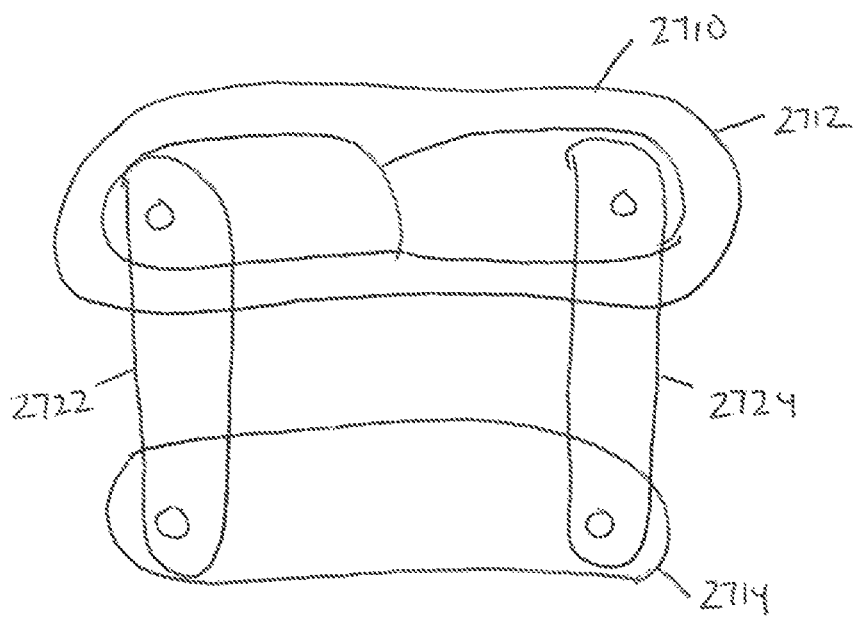

FIGS. 47A and 47B show an expandable spacer having upper and lower members separated by linking members in accordance with some embodiments. The expandable spacer 2710 comprises an upper member 2712 and a lower member 2714. FIG. 47A shows the upper member 2712 and the lower member 2714 in a first initial configuration whereby the lower member 2714 is positioned near or adjacent to the upper member 2712. To separate the lower member 2714 from the upper member 2712 and form a larger footprint, the lower member 2714 can be moved away from the upper member 2712 via linking members 2722 and 2724. In some embodiments, the linking members 2722, 2724 can be moved by moving respective pins 2732, 2734 along slots 2742, 2744 formed in the upper member 2712. In other embodiments, the lower member 2714 can be moved away from the upper member 2712 via a gear mechanism, such as a gear drive (e.g., a worm gear).

Figure 48B:
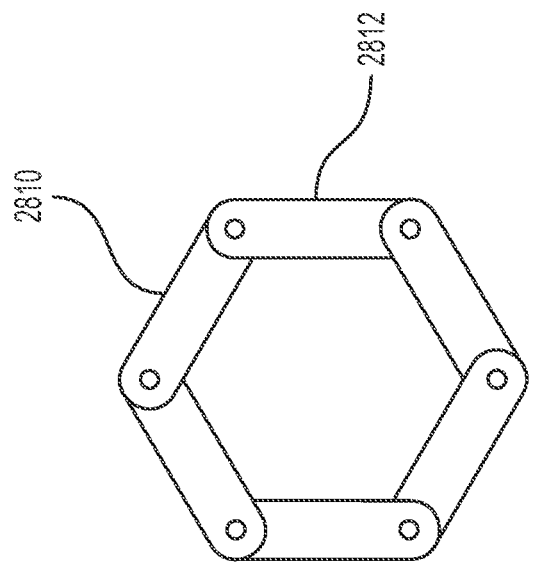
FIGS. 48A and 48B show an expandable spacer comprising a worm gear in accordance with some embodiments.
Figure 48A:
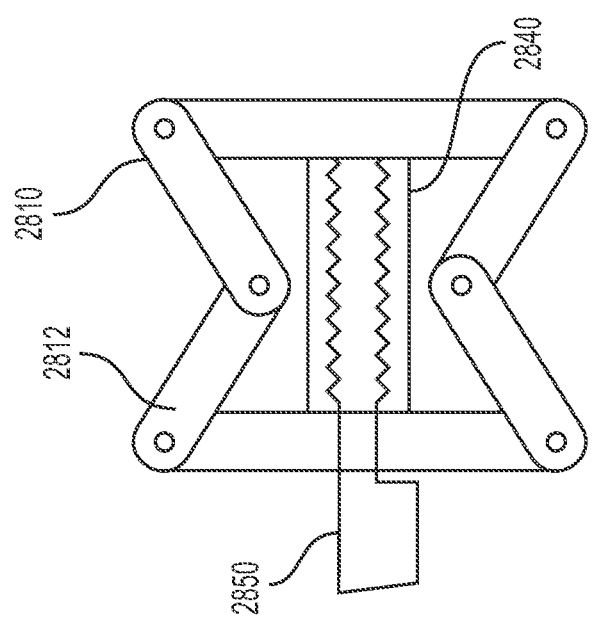

FIGS. 48A and 48B show an expandable spacer comprising a worm gear in accordance with some embodiments. The expandable spacer 2810 comprises six linking members 2812 that can expand via a worm gear 2840. The worm gear 2840 can be engaged by an instrument 2850, such as a worm drive. Rotation of the instrument 2850 causes actuation of the worm gear 2840, thereby causing expansion of the linking members 2812. As shown in FIG. 48B, the expandable spacer 2810 can be expanded such that it forms a ring member having a larger footprint than its initial configuration. In some embodiments, the worm gear 2840 can be built into the spacer 2810, while in other embodiments, the worm gear 2840 can be removeably attached to the spacer 2810.

FIGS. 49A and 49B show an expandable spacer having asymmetrical expansion in accordance with some embodiments. The spacer 2910 includes five different linking members 2912, 2913, 2914, 2915 and 2916 that are connected to one another via a joint or hinge. In some embodiments, the linking members can be connected to one another via a click fit. FIG. 49A shows the spacer 2910 in its initial, non-expanded configuration and attached to an instrument 2930. The instrument 2930 can deliver the spacer 2910 into a disc space, whereby the spacer 2910 can be pulled in the direction 2922, thereby causing expansion of the spacer 2910, as shown in FIG. 49B. Advantageously, expansion of the spacer 2910 can be asymmetrical to accommodate a desirable footprint within a disc space.

The described embodiments are capable of insertion into a disc space, and subsequent expansion. In some embodiments, the implants will be expanded into a desirable lordotic form. In some embodiments, the implants will be expanded such that the footprint is increased. The implants can be expanded such that they rest on an apophyseal ring of a patient. While the above descriptions describe numerous embodiments, one skilled in the art will appreciate that any of the embodiments discussed above are unique and novel features that may be combinable with one another.

While the invention herein disclosed has been described by means of specific embodiments and applications thereof, numerous modifications and variations can be made thereto by those skilled in the art without departing from the scope of the invention as set forth in the claims.

What is claimed is:

1. An expandable interbody spacer system comprising:
   a first jointed arm comprising a first plurality of links coupled end to end;

a second jointed arm comprising a second plurality of links coupled end to end;

an elongate screw having a head portion positioned outside of the first and second jointed arms and an elongate body, the head portion having a proximal end, a distal end, and a curved outer surface in between the proximal end and the distal end; and an insertion tool for inserting the expandable interbody spacer into an intervertebral space and having first and second tool arms configured to engage a groove disposed around the curved outer surface of the head portion to secure the insertion instrument to the expandable interbody spacer, wherein the first jointed arm and the second jointed arm are interconnected at a proximal end of the expandable interbody spacer, wherein the first jointed arm and the second jointed arm are interconnected at a distal end of the expandable interbody spacer, and wherein the first jointed arm and the second jointed arm are each configured to move in opposite directions to place the expandable interbody spacer in an expanded position.

2. The expandable interbody spacer system of claim 1, wherein the expandable interbody spacer further comprises a proximal connection member interconnecting the first and second jointed arms, wherein a proximal end of each of the first and second jointed arms is coupled to the proximal connection member.

3. The expandable interbody spacer system of claim 2, wherein the proximal connection member comprises a bore that communicates with a hollow interior portion of the expandable interbody spacer defined by the first and second jointed arms, the hollow interior portion extending axially through the expandable interbody spacer.

4. The expandable interbody spacer system of claim 1, wherein the expandable interbody spacer further comprises a distal connection member interconnecting the first and second jointed arms, wherein a distal end of each of the first and second jointed arms is coupled to the distal connection member.

5. The expandable interbody spacer system of claim 1, wherein the first jointed arm comprises upper and lower surfaces defined by the first plurality of links configured to engage adjacent vertebrae, and wherein the second jointed arm comprises upper and lower surfaces defined by the second plurality of links configured to engage adjacent vertebrae.

6. The expandable interbody spacer system of claim 1, wherein the expandable interbody spacer has a width of about 8 mm to about 22 mm prior to expansion and a width of about 26 mm to about 42 mm after expansion.

7. The expandable interbody spacer system of claim 1, wherein the first plurality of links comprises three links, and wherein the second plurality of links comprises three links, wherein washers are disposed between adjacent ones of the links.

8. The expandable interbody spacer system of claim 1, wherein one of the first plurality of links of the first jointed arm comprises a first link segment coupled to a second link segment, the first link segment and the second link segment having a tongue-and-groove connection.

9. The expandable interbody spacer system of claim 1, comprising an internal screw extending axially through the expandable interbody spacer from a proximal end to a distal end.

10. The expandable interbody spacer system of claim 1, wherein an exterior sidewall of at least one of the second plurality of links is straight and transitions into a second rounded portion.

11. An expandable interbody spacer system comprising:

a first jointed arm comprising a first plurality of links coupled end to end, wherein the first plurality of links define upper and lower surfaces configured to engage adjacent vertebrae, wherein an exterior sidewall of at least one of the first plurality of links is straight and transitions into a rounded portion;

a second jointed arm comprising a second plurality of links coupled end to end, wherein the second plurality of links define upper and lower surfaces configured to engage adjacent vertebrae, wherein an exterior sidewall of at least one of the second plurality of links is straight; and an elongate body extending through a proximal end, into an interior region, and into a distal end of the interbody spacer, wherein the elongate body is configured to expand the interbody spacer, the elongate body including a head portion having a proximal end, a distal end, and a curved outer surface in between the proximal end and the distal end of the head portion; and an insertion tool for inserting the expandable interbody spacer into an intervertebral space and having first and second tool arms configured to engage a groove disposed around the curved outer surface of the head portion to secure the insertion instrument to the expandable interbody spacer, wherein the first jointed arm and the second jointed arm are interconnected at the proximal end and the distal end of the interbody spacer.

12. The expandable interbody spacer system of claim 11, wherein the interior region is a hollow interior portion defined by the first and second jointed arms.

13. The expandable interbody spacer system of claim 12, wherein the second jointed arm comprises an opening that extends through the rounded portion of the spacer.

14. The expandable interbody spacer system of claim 13, wherein the opening faces inward into the spacer and does not extend entirely through the second jointed arm.

15. The expandable interbody spacer system of claim 11, wherein the upper and lower surfaces of the first jointed arm comprise texturing to aid in gripping the vertebrae, and wherein the upper and lower surfaces of the second jointed arm comprise texturing to aid in gripping the vertebrae.

* * * * *